(12) United States Patent
Poitzsch et al.

(10) Patent No.: US 6,366,089 B1
(45) Date of Patent: Apr. 2, 2002

(54) NUCLEAR MAGNETIC RESONANCE LOGGING WITH AZIMUTHAL RESOLUTION

(75) Inventors: Martin E. Poitzsch, Sugar Land; Peter Speier, Stafford; Krishnamurthy Ganesan; Shu-Kong Chang, both of Sugar Land; Jaideva C. Goswami, Houston, all of TX (US)

(73) Assignee: Schlumberger Technology Corporation, Houston, TX (US)

( * ) Notice: Subject to any disclaimer, the term of this patent is extended or adjusted under 35 U.S.C. 154(b) by 0 days.

(21) Appl. No.: 09/644,933

(22) Filed: Aug. 23, 2000

Related U.S. Application Data

(60) Division of application No. 09/094,201, filed on Jun. 9, 1998, which is a continuation-in-part of application No. 08/880,343, filed on Jun. 23, 1997, now Pat. No. 5,977,768.

(51) Int. Cl.[7] .................................................. G01V 3/00
(52) U.S. Cl. .......................... 324/303; 324/300; 324/322
(58) Field of Search ................................ 324/303, 300, 324/309, 306, 307, 322

(56) References Cited

U.S. PATENT DOCUMENTS 5,629,623 A * 5/1997 Sezginer et al. ............ 324/303
5,923,167 A * 7/1999 Chang et al. ................ 324/303
6,184,681 B1 * 2/2001 Heisler et al. ............... 324/303

FOREIGN PATENT DOCUMENTS

GB    2 310 500 A    8/1997

* cited by examiner

Primary Examiner—Jay Patidar
Assistant Examiner—Brij B. Shrivastav
(74) Attorney, Agent, or Firm—John J. Ryberg; Brigitte L. Jeffery

(57) ABSTRACT

The present invention relates generally to an apparatus and method for obtaining an azimuthally resolved nuclear magnetic resonance measurement of an earth formation traversed by a borehole. The measurement can be made while drilling or using a wireline tool. A receiving rf antenna having a non-axisymmetric response pattern is used to obtain the azimuthally resolved nuclear magnetic resonance measurement. The antenna employs axial currents which excite an azimuthally oriented rf magnetic field. For this situation, the static magnetic field is either radial or axial in its orientation. The antenna generates a relatively long, in axial extent, region of generally uniform static field magnitude and polarization in the formation. The present invention facilitates low profile antenna configurations that can permit dispensing with the reduction of the inner diameter of the drill collar at the rf antenna location.

12 Claims, 16 Drawing Sheets

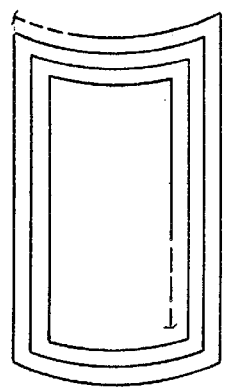
FIG. 26
FIG. 27
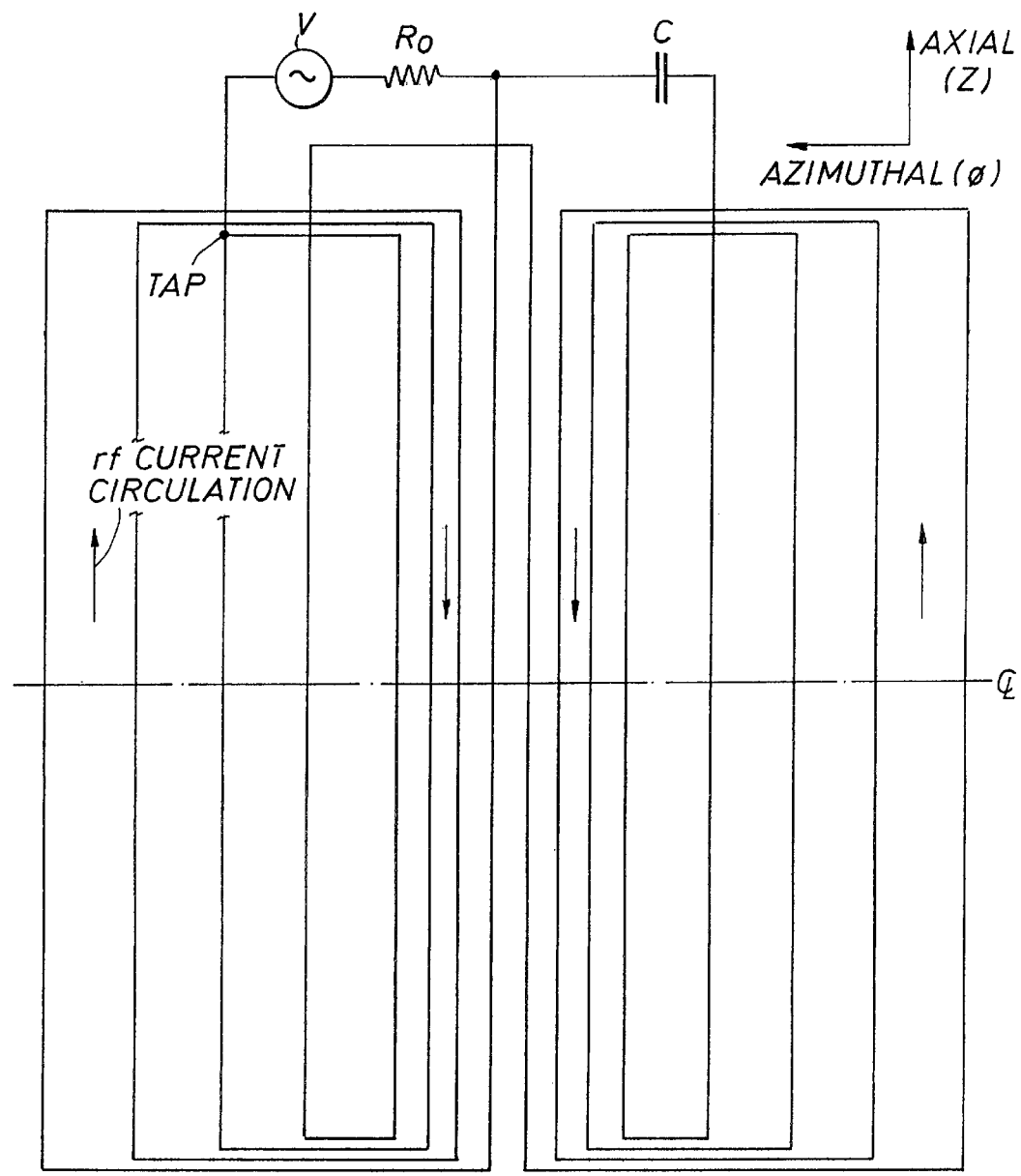

NUCLEAR MAGNETIC RESONANCE LOGGING WITH AZIMUTHAL RESOLUTION

This is a division of U.S. patent application Ser. No. 09/094,201, filed Jun. 9, 1998 which is a continuation-in-part of U.S. patent application Ser. No. 08/880,343, filed Jun. 23, 1997, now U.S. Pat. No. 5,977,768, issue date Nov. 2, 1999.

FIELD OF THE INVENTION

This invention relates to the field of well logging and, more particularly, to a method and apparatus for determining nuclear magnetic resonance logging characteristics of earth formations surrounding a borehole, either during or after the drilling of the borehole.

BACKGROUND OF THE INVENTION

In the evaluation of earth boreholes drilled in earth formations to produce hydrocarbons, determination of the porosity of the formations is considered essential for decision making. Nuclear magnetic resonance ("NMR") provides a means of measuring total and producible porosity of earth formations. In certain conditions NMR well logging can provide important information on the pore size of formation rock and on the type of fluid contained therein. Measurement of nuclear resonance requires a static magnetic field $\overline{B}_0$ and a radio frequency (RF) magnetic field in the earth formation that is being probed. [As used herein, an RF field generally has a frequency in the range 2 KHz to 10 MHz.] Atomic nuclei with a nonzero nuclear magnetic moment and spin angular momentum precess about the static field $\overline{B}_0$ with an angular frequency $\omega_0 = \gamma B_0$ when perturbed from their thermal equilibrium. The constant $\gamma$ is the gyromagnetic ratio of the resonating nucleus, most commonly the hydrogen nucleus. For hydrogen nuclei, the gyromagnetic ratio is $2.675198775 \times 10^8$ radian/second/Tesla. To manipulate the spin state of the particles, for example, to perturb the thermal equilibrium, a radio frequency (RF) magnetic field $\overline{B}_1$ is needed. The frequency of the RF field $\overline{B}_1$ should be close to $\omega_0$ and substantially perpendicular to the static field $\overline{B}_0$ in the region of investigation. Magnetic resonance is observed by detecting the oscillating magnetic field produced by the precession of the spins. Typically, but not necessarily, the same coil that produces the RF field $\overline{B}_1$ is used for detection. In pulsed-NMR, repeated pulses are applied to the coil and spin-echoes are detected in between the transmitted pulses. Reference can be made, for example, to U.S. Pat. Nos. 5,376,884, 5,055,788, 5,055,787, 5,023,551, 4,933,638, and 4,350,955 with regard to known nuclear magnetic resonance logging techniques.

In-logging-while-drilling, the measurement apparatus is mounted on a drill collar. Drill collars are long, tubular pieces of a strong material, typically nonmagnetic stainless-steel. Drill collars and drill pipes transmit the torque from the surface apparatus to the drill bit. During drilling, the drill collars typically rotate about their axes, which are substantially aligned with the axis of the borehole. The rates of rotation of the drill collars and the drill bit are the same in rotary drilling, and can be different if a downhole mud motor is used. In either case, the drill collar is subject to rotation. For logging-while-drilling NMR logging, the magnitudes of $\overline{B}_0$, $\overline{B}_1$, and the angle between them should be substantially invariant of the rotation angle in the region of investigation. This does not preclude the possibility that the directions of $\overline{B}_0$ and $\overline{B}_1$ may depend on the rotation angle. The foregoing invariance is required because magnetic resonance measurements take on the order of 0.01 to 1 seconds during which the drill collar may rotate by a substantial angle. Consistent preparation and measurement of spin states are not possible without the rotational invariance.

Directional drilling involves the drilling of a well bore along a deviated course in order to reach a target region at a particular vertical and horizontal distance from the original surface location. Directional drilling is employed, for example, to obtain an appropriate well bore trajectory into an oil producing formation bed (or "pay zone") and then drill substantially within the pay zone. A horizontally drilled well can greatly increase the borehole volume in the pay zone with attendant increase in oil production. Recent advances in directional drilling equipment and techniques have greatly improved the accuracy with which drilling paths can be directed.

Nuclear magnetic resonance logging systems have previously been proposed for logging-while-drilling applications. If an NMR logging device of a logging-while-drilling system has an axially symmetric response, the NMR characteristics measured by the logging device will tend to average the signals received circumferentially from the formations. For example, when drilling a near-horizontal well along the boundary between two formation beds with dissimilar producible porosities, such a logging device would give indication of an intermediate porosity. It would be very advantageous to be able to use NMR to better delineate the presence, locations, and characteristics of the formation beds in this type of a situation.

It is among the objects of the present invention to address limitations of the prior art with regard to nuclear magnetic resonance logging techniques and apparatus.

SUMMARY OF THE INVENTION

The invention described in the copending parent application hereof, U.S. application Ser. No. 08/880,343, provides the capability of azimuthally resolved nuclear magnetic resonance logging. That invention and the invention hereof can both be used in so-called wireline logging, but the inventions are particularly advantageous in achieving azimuthally resolved NMR logging-while-drilling measurements.

A form of the invention set forth in said copending U.S. application Ser. No. 08/880,343 is directed to an apparatus and method for determining a nuclear magnetic resonance property of formations surrounding a borehole while drilling the borehole with a rotating drill bit on a drill string. An embodiment of the method of that invention includes the following steps: providing a logging device in the drill string, the logging device being rotatable with the drill string or a portion of the drill string, the logging device having a rotational axis; producing a static magnetic field and an RF magnetic field at the logging device, the static and RF magnetic fields having mutually orthogonal components in an investigation region in the formations surrounding the logging device, the magnitudes of the static and RF magnetic fields in the investigation region being substantially rotationally invariant as the logging device rotates around its axis; receiving nuclear magnetic resonance spin echoes at at least one circumferential sector on the logging device; and determining a nuclear magnetic resonance property of the formations, for different portions of the investigation region, from the received nuclear magnetic resonance spin echoes. [It will be understood that the static and RF magnetic fields are defined as having "mutually orthogonal components" if they are not parallel. Typically, but not necessarily, the static and RF magnetic fields will be substantially perpendicular in the investigation region.]

In another form of the invention set forth in said copending Application, the receiving of nuclear magnetic resonance spin echoes is implemented at a plurality of different circumferential sectors on the logging device and comprises providing a plurality of arcuate receiver segments-around the logging device and detecting nuclear magnetic resonance spin echoes in signals received by the individual receiver segments.

In embodiments hereof, in order to make an azimuthally-resolved NMR measurement, the receiving radio-frequency antenna has a non-axisymmetric response pattern. The transmitting (pulsing) antenna can be either the same non-axisymmetric antenna, or a separate non-axisymmetric antenna, or a separate axisymmetric antenna. If the azimuthal measurement is to be performed while the tool is rotating (as is typically the case in MWD), the static magnetic field ($\overline{B}_0$) should be axisymmetric, at least in terms of its magnitude. In certain embodiments hereof, the rf antennas employ axial currents (parallel to the tool and wellbore axis), which excite an azimuthally-oriented rf magnetic field ($\overline{B}_1$). For this situation, the static magnetic field ($\overline{B}_0$) should be either radial or axial in its orientation, so as to be approximately perpendicular to the azimuthal $\overline{B}_1$ field excited by the rf antenna, as is desirable for efficient NMR signal generation and reception. In another embodiment, the rf antenna excites a radially-oriented rf magnetic field. In this case, the static magnetic field should be either axial, transverse, or azimuthal in its orientation. In embodiments of the invention to be described, a region of generally uniform static field magnitude and polarization produced in the formations is relatively long in axial extent, and an advantage is that the rf antenna used to obtain azimuthally resolved measurements can also be made relatively long in the axial direction, thereby increasing the volume of spins ultimately sensed by the antenna and increasing signal-to-noise ratio. This increase tends to offset the decrease in the volume of spins that are detected when the azimuthal range of investigation is limited to a sector that is a fraction of a full circumference.

A form of the invention is a method for determining a nuclear magnetic resonance property of formations surrounding a borehole during a drilling operation in the borehole with a drill string, comprising the following steps: providing a logging device in the drill string, the logging device having a longitudinal axis; producing, from said logging device, a static magnetic field and an rf magnetic field in the formations; and receiving nuclear magnetic resonance signals from an investigation region of the formations at an antenna having a response pattern that is non-axisymmetric, said response pattern having an azimuthal polarization in the investigation region.

In accordance with an embodiment of apparatus in accordance with the invention, there is disclosed an apparatus for determining a nuclear magnetic resonance property of formations surrounding a borehole which comprises: a logging device moveable through the borehole; means in said logging device for producing a static magnetic field in the formations; and antenna means in said logging device for producing an rf magnetic field in the formations, and for detecting nuclear magnetic resonance signals from the formations, the antenna means including a plurality of spaced apart generally cylindrical arc-shaped conductors, and means coupled across the arc-shaped conductors for detecting signals induced in the conductors. In a preferred embodiment of this form of the invention, the logging device has a longitudinal axis, and the cylindrical arcs of the conductors are concentric with said axis. In this embodiment, the means for producing an rf magnetic field in said formations is operative to generate current flowing in adjacent conductors in opposing axial directions and the means for detecting signals is operative to detect currents flowing in adjacent conductors in opposing axial directions.

In another embodiment of the invention, the antenna means includes at least one multi-turn current loop having an axis that is substantially perpendicular to the longitudinal axis of the logging device, and means coupled with said current loop for detecting signals induced in said current loop. In a preferred form of this embodiment, the at least one multi-turn current loop is formed in a generally cylindrical arc shape, said arc being centered on a line oriented in the direction of the longitudinal axis.

In embodiments of the invention, an antenna is low profile and can be formed in an outer groove in the drill collar without necessarily reducing the inner diameter of the drill collar, which is ordinarily done to increase strength in a region of drill collar where the outer diameter has been recessed to provide an antenna. [The reduction in the bore size of the drill collar is preferably avoided, if possible, as it requires extra machining of the drill collar and contributes to constriction of mud flow.] In accordance with these embodiments there is disclosed an apparatus for nuclear magnetic resonance logging that is mountable in a drill string for logging of formations surrounding a borehole, comprising: a tubular drill collar having a generally cylindrical inner surface having an inner diameter and a generally cylindrical outer surface having an outer diameter; first means in the drill collar for producing a first magnetic field; second means in the drill collar for producing a second magnetic field; and means in the drill collar for receiving nuclear magnetic resonance signals from an investigation region in the formations; the second means comprising an antenna disposed in a recess spanning an axial extent in the outer cylindrical surface, the outer surface of said-drill collar having a diameter that is reduced from the outer diameter over the axial extent of the recess, and the inner surface of the drill collar having a diameter that is not reduced from the inner diameter over the axial extent of the recess. In a form of this embodiment, the antenna comprises at least one generally cylindrical arc-shaped conductor plate in the recess. In another form of this embodiment, the antenna comprises at least one multi-turn loop formed in a generally cylindrical arc shape in the recess.

Further-features and advantages of the invention will become more readily apparent from the following detailed description when taken in conjunction with the accompanying drawings.

BRIEF DESCRIPTION OF THE DRAWINGS

FIG. 26 illustrates a spirally wound multi-turn loop antenna in an arc shaped configuration.

FIG. 27 illustrates a twin-loop multi-turn planar loop antenna in accordance with an embodiment of the invention and which can be used in practicing an embodiment of the method of the invention.

DETAILED DESCRIPTION

Figure 1:
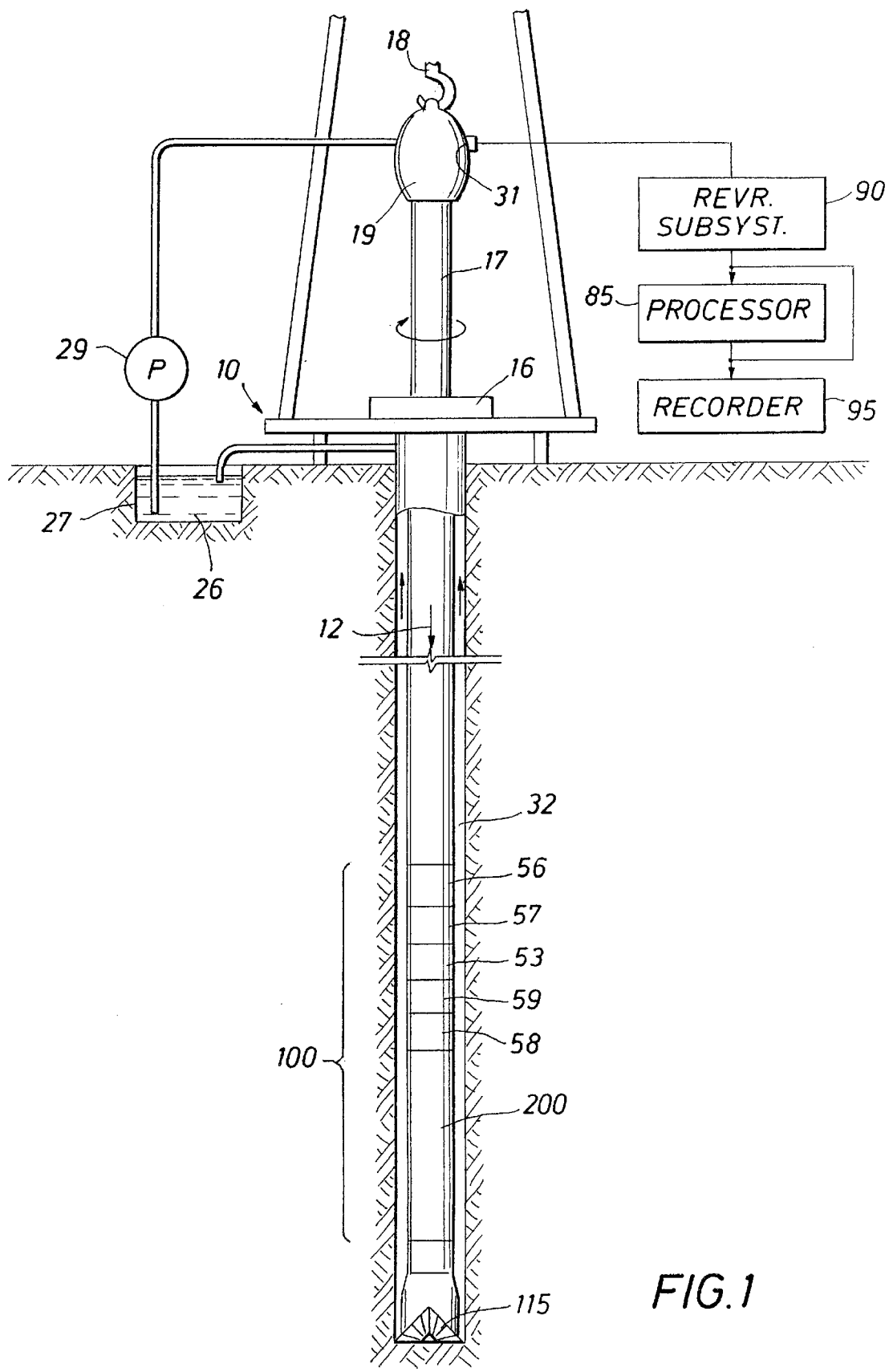
FIG. 1 is a diagram of a logging-while-drilling system in which an embodiment of the invention can be utilized-and which can be used in practicing the method of the invention.

Referring to FIG. 1, there is illustrated a logging-while-drilling apparatus and method in which embodiments of the invention can be practiced. A platform and derrick 10 are positioned over a borehole 32 that is formed in the earth by rotary drilling. A drill string 12 is suspended within the borehole and includes a drill bit 115 at its lower end. The drill string 12, and the drill bit 115 attached thereto, is rotated by a rotating table 16 (energized by means not shown) which engages a kelly 17 at the upper end of the drill string. The drill string is suspended from a hook 18 attached to a traveling block (not shown). The kelly is connected to the hook through a rotary swivel 19 which permits rotation of the drill string relative to the hook. Alternatively, the drill string may be rotated from the surface by a "top drive" type of drilling rig. Drilling fluid or mud 26 is contained in a pit 27 in the earth. A pump 29 pumps the drilling fluid into the drill string 12 via a port in the swivel 19 to flow downward through the center of drill string 12. The drilling fluid exits the drill string via ports in the drill bit 115 and then circulates upward in the region between the outside of the drill string and the periphery of the borehole. As is well known, the drilling fluid thereby carries formation cuttings to the surface of the earth, and the-drilling fluid is returned to the pit 27 for recirculation. The small arrows in the Figure illustrate the typical direction of flow of the drilling fluid.

Mounted within the drill string 12, preferably near the drill bit 115, is a downhole sensing, processing, storing and transmitting subsystem 100. Subsystem 100 includes a measuring apparatus 200 in accordance with an embodiments of the invention which are illustrated hereafter. Also provided in the downhole subsystem is a device or tool 59, of a type known in the art, for measuring and/or computing the direction and inclination of the bottom hole assembly and the rotational orientation of the bottom hole assembly ("tool face"). Reference can be made, for example, to U.S. Pat. No. 5,473,158. A communications transmitting portion of the downhole subsystem includes an acoustic transmitter 56, which generates an acoustic signal in the drilling fluid that is representative of the measured-downhole conditions. One suitable type of acoustic transmitter, which is known in the art, employs a device known as a "mud siren" which includes a slotted stator and a slotted rotor that rotates and repeatedly interrupts the flow of drilling fluid to establish a desired acoustic wave signal in the drilling fluid. The generated acoustic-mud wave travels upward in the fluid through the center of the drill string at the speed of sound in the fluid. The acoustic wave is received at the surface of the earth by transducers represented by reference numeral 31. The transducers, which are, for example, piezoelectric transducers, convert the received acoustic signals to electronic signals. The output of the transducers 31 is coupled to the uphole receiver subsystem 90 which is operative to demodulate the transmitted signals, which are then coupled to processor 85 and recorder 95.

Transmitter 56 can be controlled by conventional transmitter control and driving electronics 57 which includes analog-to-digital (A/D) circuitry that converts (if necessary) the signals representative of downhole conditions into digital form. The control and driving electronics 57 may also include a suitable modulator, such as a phase shift keying (PSK) modulator, which conventionally produces driving signals for application to the transmitter 56. These driving signals can be used to apply appropriate modulation to the mud siren of transmitter 56. It will be understood that alternative techniques can be employed for communicating logging information to the surface of the earth.

Figure 4:
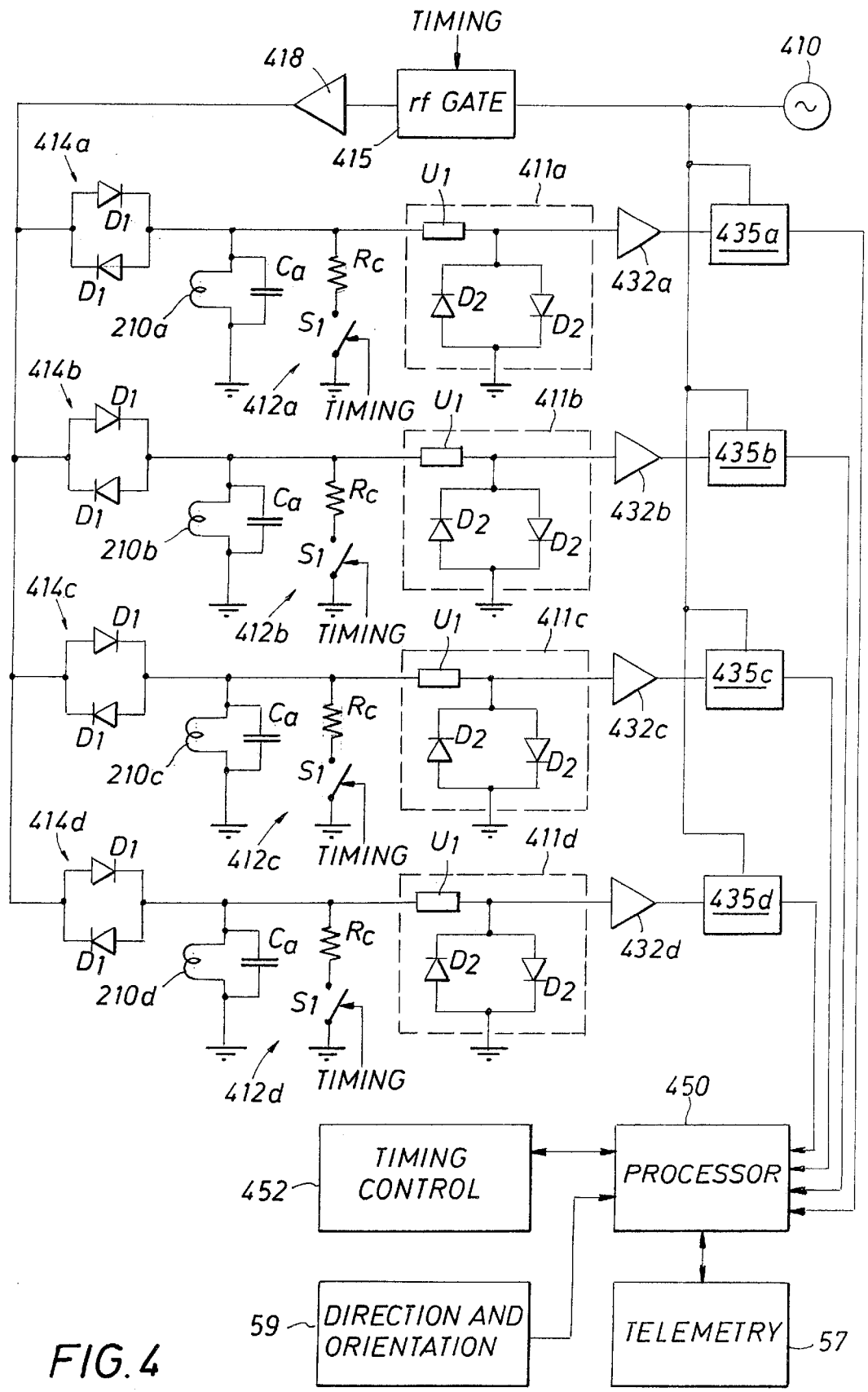
FIG. 4 is a block diagram of circuitry used in an embodiment of the invention-as set forth in the above-referenced copending U.S. patent application Ser. No. 08/880,343.

The downhole subsystem 100 further includes acquisition and processor electronics 58, which can include electronics as shown in FIG. 4. The acquisition and processor electronics 58 are coupled to the measuring apparatus 200 and obtain measurement information therefrom. In known manner, the acquisition and processor electronics is capable of storing data from the measuring apparatus, processing the data and storing the results, and coupling any desired portion of the information it contains to the transmitter control and driving electronics 57 for transmission to the surface by transmitter 56. A battery 53 may provide downhole power. As known in the art, a downhole generator (not shown) such as a so-called "mud turbine" powered by the drilling fluid, can also be utilized to provide power during drilling.

If desired, the drilling equipment can be a directional drilling equipment. Such equipment (not shown) typically includes an offset (or "bent") sub, a mud motor that is driven by the flowing mud. The mud motor and bent sub can alternatively be combined in a mud motor unit upper portion of the housing and bearings in the bottom portion of the housing, with the motor drive in the upper portion of the housing and bearings in the bottom portion of the housing. The bent sub or bent housing typically has an offset or bend angle of ½ to 2 degrees. As is known in the art, when the bit is driven by the mud motor only (with the drill string not rotating), the bit will deviate in a direction determined by the tool face direction in which the drill string and bent sub are oriented [so-called "sliding model"]. When it is desired to drill substantially straight, the drill string containing the mud motor is rotated [so-called "rotating mode"].

Figure 2:
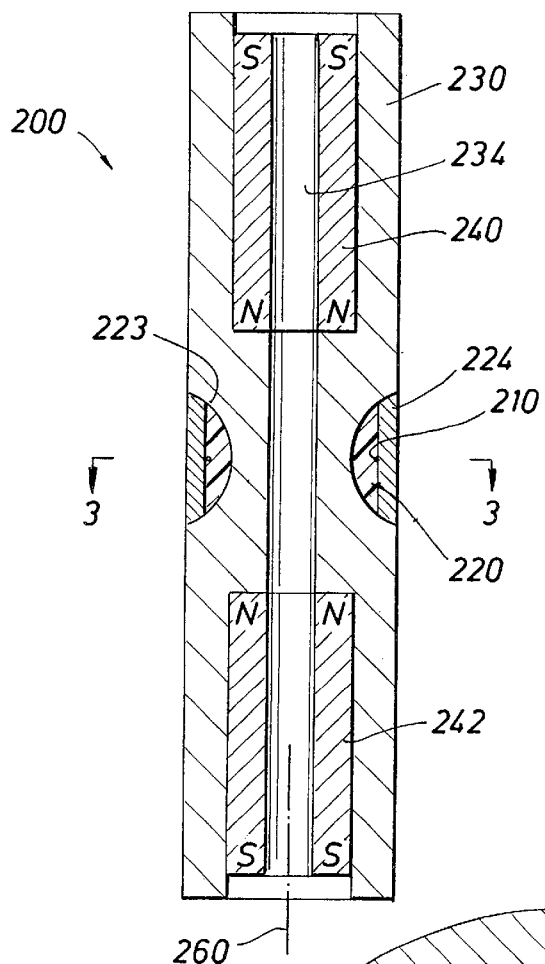
FIG. 2 is a cross-sectional view of a logging device in accordance with an embodiment of the invention as set forth in the above-referenced copending U.S. patent application Ser. No. 08/880,343.

FIG. 2 illustrates a form of the downhole measuring apparatus 200 (of FIG. 1) in accordance with an embodiment of the invention as set forth in the above-referenced copending U.S. patent application Ser. No. 08/880,343. The tool 200 is rotationally symmetric about axis 260 of the drill collar 230 in which the tool is constructed, and which is substantially aligned with the axis of the borehole. The static magnetic field $\overline{B}_0$ is produced by tubular, axially polarized, permanent magnets 240 and 242 mounted inside the drill collar 230. Channel 234 located inside the tool and the magnets, permits drilling mud to flow toward the drill bit. In the region between the permanent magnets, the drill collar has a circumferential recess 223 which, in the present embodiment, has an arcuate cross-section. A segmented antenna 210 is provided in the recess 223. A non-conductive material 220 is provided in the recess beneath the antenna. The material 220 is preferably a ferrite to increase the efficiency of the antenna. The antenna is protected from the abrasion and impact of the drilling environment by a shield 224, which can comprise a slotted metallic tube and/or insulating material.

Figure 3:
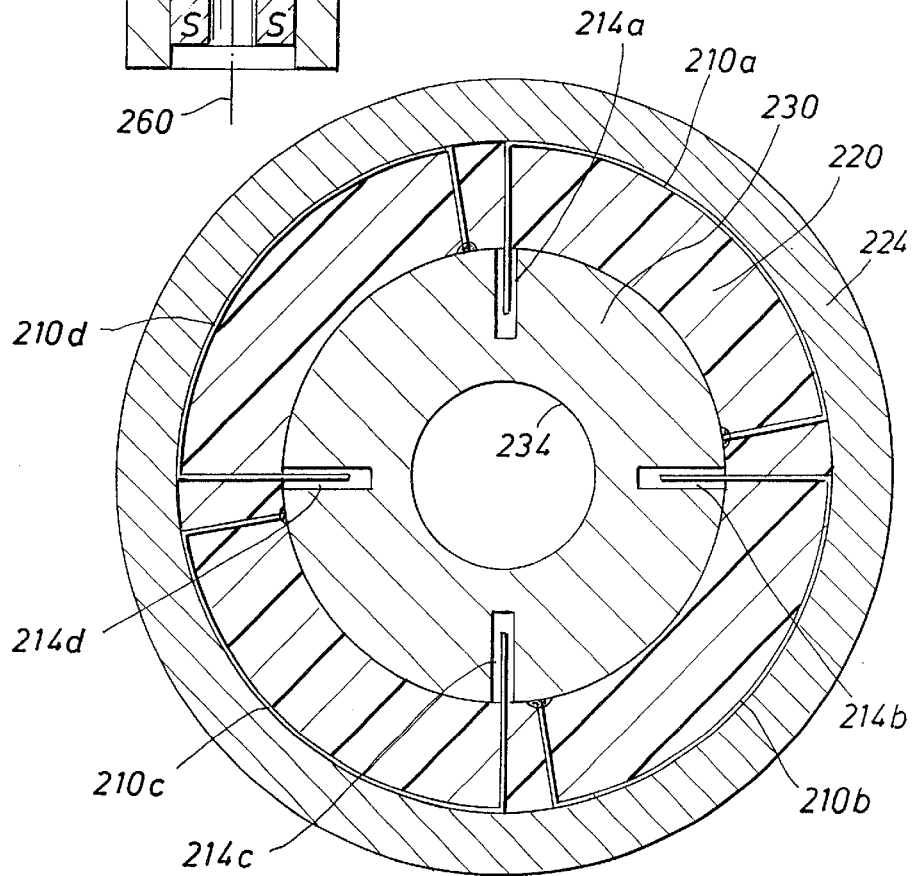
FIG. 3 is a cross-sectional view of the logging device of FIG. 2 as taken through a section defined by the arrows 3—3 of FIG. 2.

FIG. 3 is a cross-sectional view through a section of the logging device that includes the antenna 210 which, in the illustrated embodiment, as set forth in the above-referenced copending U.S. patent application Ser. No. 08/880,343, has a plurality of segments, and is used for both transmitting and receiving. In this embodiment there are four antenna segments, labeled 210a, 210b, 210c and 210d. Each segment is a circumferential sector that is approximately a quadrant of a one turn coil, and has one end at ground reference potential, which can be coupled with the drill collar. The other end of each coil segment passes through a respective feed-through slot (labeled 214a, 214b, 214c, and 214d), each of which runs lengthwise through the drill collar, and the respective wiring is coupled to circuitry in the module 58, which is shown in further detail in FIG. 4.

In the circuit block diagram of FIG. 4, as set forth in the above-referenced copending U.S. patent application Ser. No. 08/880,343, a transmitter section includes an oscillator, represented at 410, an output of which is coupled to an rf gate 415, and then a power amplifier 418. The rf gate is under timing control of a timing block. The output of power amplifier 418 is coupled via respective extender diode circuits 414a, 414b, 414c and 414d, to the antenna segments 210a, 210b, 210c, and 210d, which are shown in FIG. 4 conjunction with respective tuning capacitances $C_a$, $C_b$, $C_c$ and $C_d$. Each of the extender diode circuits 414a, 414b, 414c and 414d includes a pair of back-to-back diodes, each designated $D_1$. Also coupled with the respective coil segments 210a, 210b, 210c and 210d are respective Q-switch circuits 412a, 412b, 412c and 412d. Each Q-switch circuit includes a critical-damping resistor $R_c$ and semiconductor switch $S_1$, for example a MOSFET. The antenna segments 210a, 210b, 210c and 210d are also coupled, via respective duplexer circuits 411a, 411b, 411c and 411d, to respective receiver circuitry that includes respective preamplifiers 432a, 432b, 432c and 432d and respective phase sensitive detectors 435a, 435b, 435c and 435d. Each of the duplexer circuits (411a–d) includes a quarter wavelength transmission line $U_1$ and an array of pairs of back-to-back diodes, each designated $D_2$, arranged as shown. Each of the phase sensitive detectors (435a–d) receives a reference signal from the oscillator 410. The outputs of the phase sensitive detectors are coupled to a downhole processor 450, which may typically be a digital processor with associated memory and input/output circuitry (not separately shown). Timing control circuitry is associated with the processor, as represented at 452, and timing control is suitably provided as illustrated in other places in the diagram.

The processor 450 also receives an input from module 59, which includes signals representative of the rotational orientation of the downhole assembly. These signals can be used to relate the NMR signals, which are measurements with respect to the device geometry, to the formation surrounding the borehole. Alternatively, the tool 200 can be provided with a dedicated subsystem for determining tool rotational orientation and performing the necessary processing, as described in U.S. Pat. No. 5,473,158. Telemetry circuitry 57 is conventionally provided for communicating with the earth's surface.

In operation, and as is known in the art, nuclear magnetic resonance circuitry can operate in three modes: transmitting, damping, and receiving. Reference can be made, for example, to U.S. Pat. Nos. 4,933,638, 5,055,787, 5,055,788, and 5,376,844. As described in the referenced patents, during the transmitting mode, the transmitter section generates relatively large rf power for a short precisely timed period, shuts off this current very quickly, within about 10 microseconds, and then isolates any signals or noise of the power circuits from coupling with detection circuitry. In the embodiment of FIGS. 2–4, as set forth in the above-referenced copending U.S. patent application Ser. No. 08/880,343, transmitting and receiving are both implemented from the plurality of coil segments. Immediately after transmitting, the purpose of the Q-switches (412a–d) is to damp the rf energy in the coil as fast as possible so that the preamplifiers 432a–d can start detecting the much smaller NMR signal as soon as possible after the rf pulse. Under timing control, the switch $S_1$ is closed to achieve this purpose. Duplexer circuits 411a–d protect preamplifiers 432a–d from the rf, pulses applied by power amplifier 418. It is important that duplexers 411a–d do not load the output of power amplifier 418. This is achieved by the quarter wavelength transmission line $M_1$ and the diodes $D_2$. When high power is applied, the diodes $D_2$ conduct and become almost short circuits. The quarter wavelength transmission line $U_1$ inverts the impedance of the diodes $D_2$. Therefore, the combination of the diodes $D_2$ and the quarter wavelength transmission line is seen as an open circuit by the power amplifier. During receiving, the signal is below the threshold voltage of the diodes $D_2$, and they appear as an open circuit. Then, the respective quarter wavelength transmission lines $U_1$ connect rf coils 210a–d to preamplifiers 432a–d. The quarter wavelength lines can be implemented by any suitable means, for example by lumped capacitors and inductors, because the length of an actual quarter wave transmission line would be impracticably long, for example 375 m at 200 kHz. The diodes $D_1$ of extender circuits 414a–d conduct only during transmission. These diodes isolate the preamplifiers 432a–d from parasitic noise and ringing that may be produced in power amplifier 418.

As above indicated, the antenna segments 210a–d are collectively used as a transmitter coil and then, during reception, as receiver segments that provide reception at different circumferential sectors on the logging device. When all segments of the coil are energized in parallel, the resulting $B_1$ field is substantially invariant with respect to rotation angle. There will be some deviation from rotational symmetry in the vicinity of the coil segments, but further away from the coils, such as in the investigation region, the field will have substantially rotational symmetry.

Figure 5:
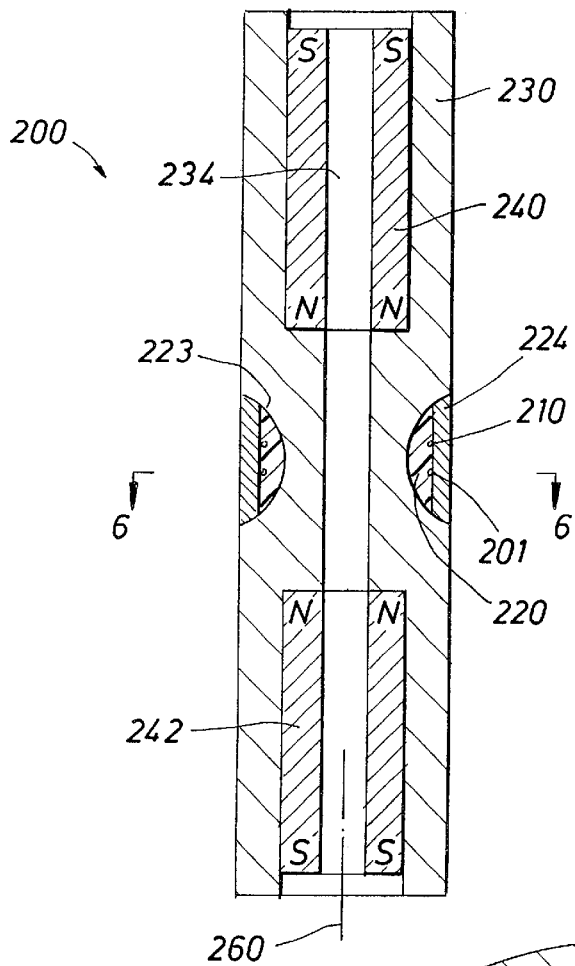
FIG. 5 is a cross-sectional view of a logging device in accordance with an embodiment of the invention as set forth in the above-referenced copending U.S. patent application Ser. No. 08/880,343.
Figure 6:
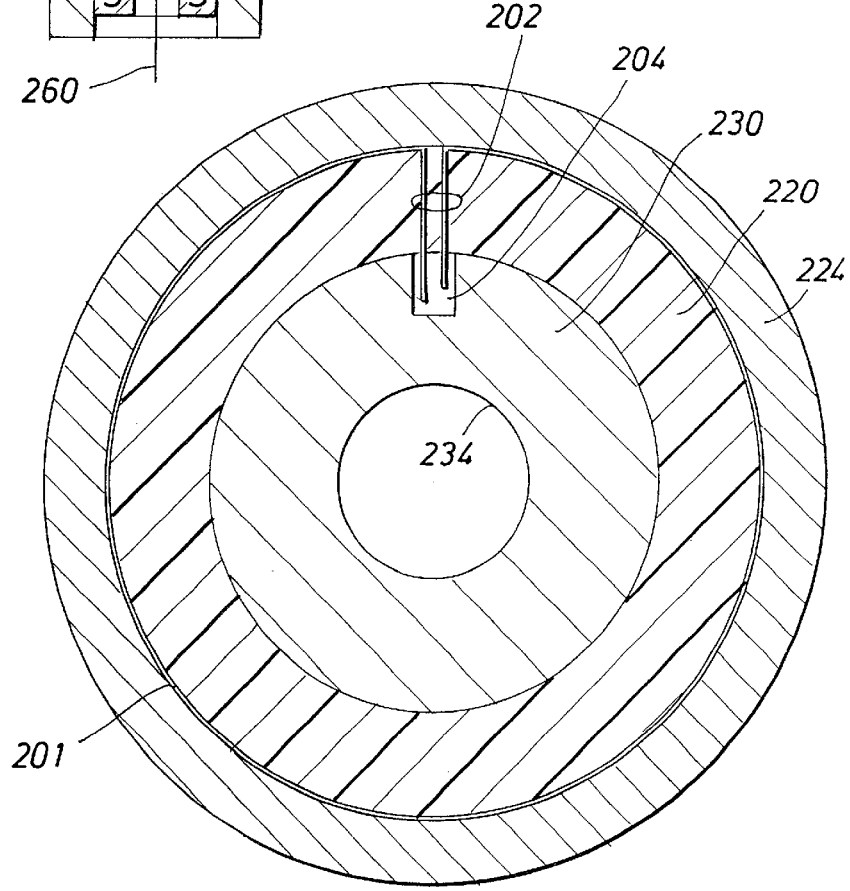
FIG. 6 is a cross-sectional view of the logging device of FIG. 5 as taken through a section defined by the arrows 6–6 of FIG. 5.
Figure 7:
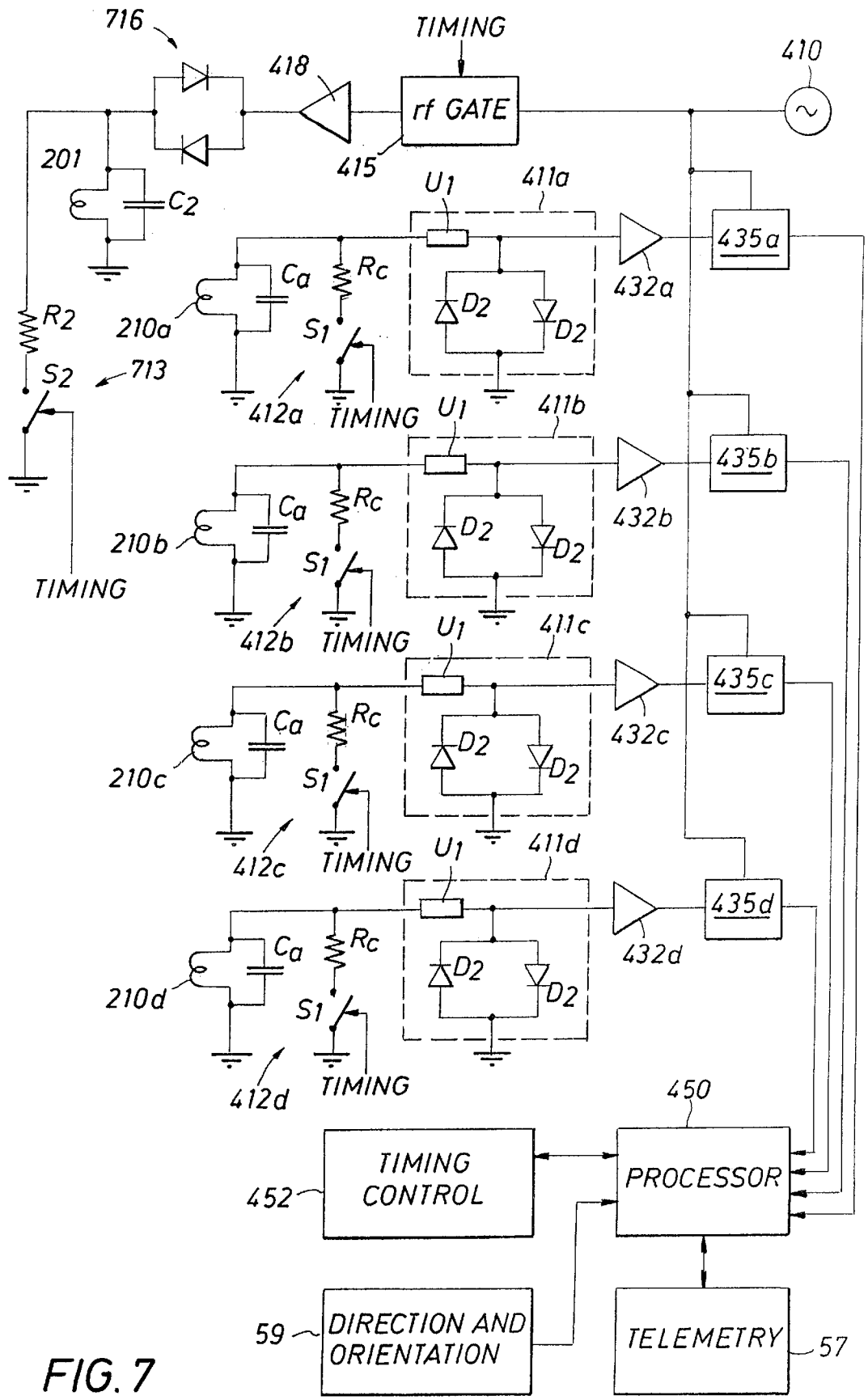
FIG. 7 is a block diagram of circuitry used in an embodiment of the invention as set forth in the above-referenced copending U.S. patent application Ser. No. 08/880,343.

FIGS. 5, 6 and 7 illustrate a further embodiment as set forth in the above-referenced copending U.S. patent application Ser. No. 08/880,343, wherein the receiver coil comprises the coil segments previously described (and represented by reference numeral 210 in FIG. 5, and reference numerals 210a, 210b, 210c and 210d in FIG. 7). FIG. 5 shows the downhole measuring apparatus, with similar components to those of FIG. 2 represented by like reference numerals. This embodiment includes a separate transmitting antenna 201 spaced from the segmented coil 210. The transmitter coil 201 is axisymmetric in construction and produces an axisymmetric rf magnetic field.

FIG. 6 is a cross-sectional view through a section of the logging device that includes the transmitting antenna 201. In this embodiment, as described in the copending U.S. patent application Ser. No. 08/880,343, the transmitting antenna is an axially symmetric single turn coil, although plural turns may be used. The wiring leads 202 for energizing the coil 201 pass through the insulating medium 220 to a feed-through slot 204 in the drill collar 230 that runs lengthwise along the drill collar, parallel to the axis thereof, to the circuitry in the module 58. The wiring in this and other feed-throughs is insulated.

FIG. 7 is a block diagram of an embodiment, as set forth in the above-referenced copending U.S. patent application Ser. No. 08/880,343, of the circuitry in the module 58 for use in conjunction with the antennas of FIG. 5, 6 embodiment. Portions of the circuitry are similar to those of the FIG. 4 embodiment and are represented by like reference numerals. In this embodiment the transmitter circuitry again includes oscillator 410, rf gate 415, and power amplifier 418, and the transmitter coil 201 (shown in parallel with tuning capacitor $C_2$) is driven via extender diode circuit 716 and has associated Q-switch 713 that comprises switch $S_2$ and critical damping resistor $R_2$. The rest of the circuitry is similar to its counterpart in FIG. 4.

Figure 8:
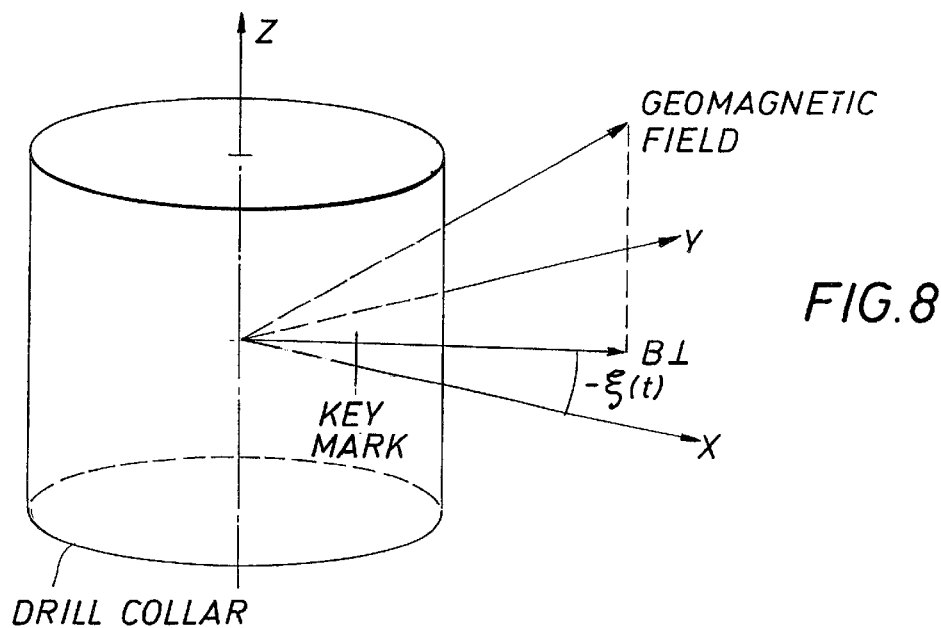
FIG. 8 is a simplified diagram of directions and orientations in the borehole that is useful in understanding an aspect-of the invention in accordance with an embodiment of the invention as set-forth in the above-referenced copending U.S. patent application Ser. No. 08/880,343.

The following analysis, as set forth in the above-referenced copending U.S. patent application Ser. No. 08/880,343, illustrates how the signals received from the different circumferential sectors can be used in conjunction with information from the direction and orientation module 59 (e.g. FIGS. 1, 4, and 7) in determining properties of different portions (e.g. different circumferential portions) of the investigation region. In the simplified diagram of FIG. 8, the axis of the drill collar is designated as the z axis. The axis z is not necessarily vertical but it is substantially in the direction of drilling. Assume that a key mark is scribed axially on the outer surface of the drill collar. This mark serves as a reference for measurement of azimuth angle around the tool (tool rotational orientation). The axis x is perpendicular to the axis z and it points radially from the axis of the drill collar to the key mark as shown in FIG. 8. The axis y is orthogonal to the axes x and z. The axes x, y, z define an orthogonal reference frame that rotates together with the tool. Magnetometers Mx and My are mounted in the drill collar so that their sensitive axes are x and y, respectively. Similarly, accelerometers Ax and Ay are mounted so that their sensitive axes are x and y, respectively. The magnetic and gravitational fields of the Earth define two azimuth directions that are fixed with respect to the Earth. Let B⊥ be the component of the geomagnetic field that is perpendicular-to the axis z of the drill collar. Similarly, let G⊥ be the component of the gravitational field that is perpendicular to the axis z of the drill collar. B⊥ points South and G⊥ points down. Either one of these directions can be used as the reference for azimuth that is fixed with respect to the earth formation. The preferred reference is the magnetic one as the measurement of acceleration can be confused by the drilling vibration since acceleration and gravitational attraction are fundamentally indistinguishable. A limitation of the described technique for determining rotational orientation is when the axis z of the drill collar, the geomagnetic field, and the gravitational field are all aligned with each other. In such case, there is a lack of an azimuth reference that is fixed with respect to the earth. This could happen, for example, in vertical wells close to the North or South Pole. The azimuth of the key mark with respect to B⊥ is ξ=atan2(−My,Mx) where atan2 is the 4-quadrant inverse tangent function defined, for example, in standard FORTRAN or C manuals or ISO 9899. Similarly, the azimuth of the key mark with respect to G⊥ is ζ=atan2(−Ay,Ax). Both of the angles ξ and ζ are time dependent when the drill string is rotating. Assume there are N receiver coils labeled n=1,2 . . . N centered at azimuths 2 πn/N on the drill collar, measured with respect to the key mark. The following components of the tool are physically aligned in azimuth: the sensitive axis of the accelerometer Ax, the sensitive axis of the magnetometer Mx, the key mark, and the center of the receiver coil N. All of these rotate together. The normalized sensitivity function of receiver n is: f(φ−2 πn/N) where φ is the azimuth angle measured with respect to the key mark on the drill collar. This function can by obtained by using a radially oriented sheet-like specimen and measuring the signal amplitude as a function of the azimuth of the radially oriented specimen. The function f is by definition periodic with period 2 π. Ideally, the sensitivity functions of the receivers is a partition of unity of design, i.e.:

$$1 = \sum_{n=1}^{N} f(\phi - 2n\pi/N) \quad (1)$$

This ensures that the receivers collectively do not have blind zones in azimuth. Since the actual sensitivity functions are smoothly varying functions of azimuth, the receivers necessarily have overlapping sensitive zones to satisfy the partition of unity. If equation (1) is not satisfied, a linear combination of the outputs of the receivers can be formed so that the linear combinations are as close as possible to a partition of unity. For a spin-echo that occurs at time instant t, the output of receiver n can be called e(t,n). Let ψ be the azimuth angle measured with respect to the direction B⊥ in the Earth. The function E(t,ψ) is the azimuthally resolved signal at time t:

$$E(t, \psi) = \sum_{n=1}^{N} e(t, n) f(\psi - \xi(t) - 2n\pi/N) \quad (2)$$

The formula (2) gives a sequence of echoes E(t,ψ) for each azimuth ψ. For each azimuth ψ, these echoes can be analyzed in the usual fashion as described, for example, in U.S. Pat. Nos. 5,363,041 and 5,389,877. In two ways, formula (2) is in agreement with common sense: First, in the event that all receivers have the same output, i.e., e(t,l)=e(t,2)= . . . =e(t,N), by partition of unity, the azimuthally resolved output E(t,ψ) becomes independent of the azimuth angle and equal to e(t,n) for any n. Second, suppose the sensitivity functions f were perfectly sharp; that is, each receiver were equally sensitive to a range of azimuth values and had no sensitivity outside this range:

$$f(\phi) = 1 \quad \text{if} \quad -\pi/N < \phi \pm \pi/N. \quad (3)$$
$$= 0 \quad \text{otherwise}$$

This assumption is not realistic because magnetic fields in the formation cannot have sharp transitions. In reality, f is a bell-shaped curve. Therefore, the azimuthal resolution is not sharp. Nevertheless, the idealization (3) above leads to a useful thought experiment. In this case, E(t,ψ) would be equal to the output of one of the receivers: E(t,ψ)=e(t,n), where n is such that ξ(t)+(2n−1)π/N<ψ≦ξ(t)+(2n+1)π/N. That is, the part of the formation that is in the ±π/N azimuthal neighborhood. of receiver coil n at the time instant t, would be assigned the reading e(t,n). This is the intended action. The sensitivity function f is actually a smoothly varying, bell-shaped curve. Therefore, the results will vary smoothly as a function of azimuth. The azimuthal resolution will be on the order of the width of the bell-shaped curve f(φ), which is about 20 π/N.

Figure 9:
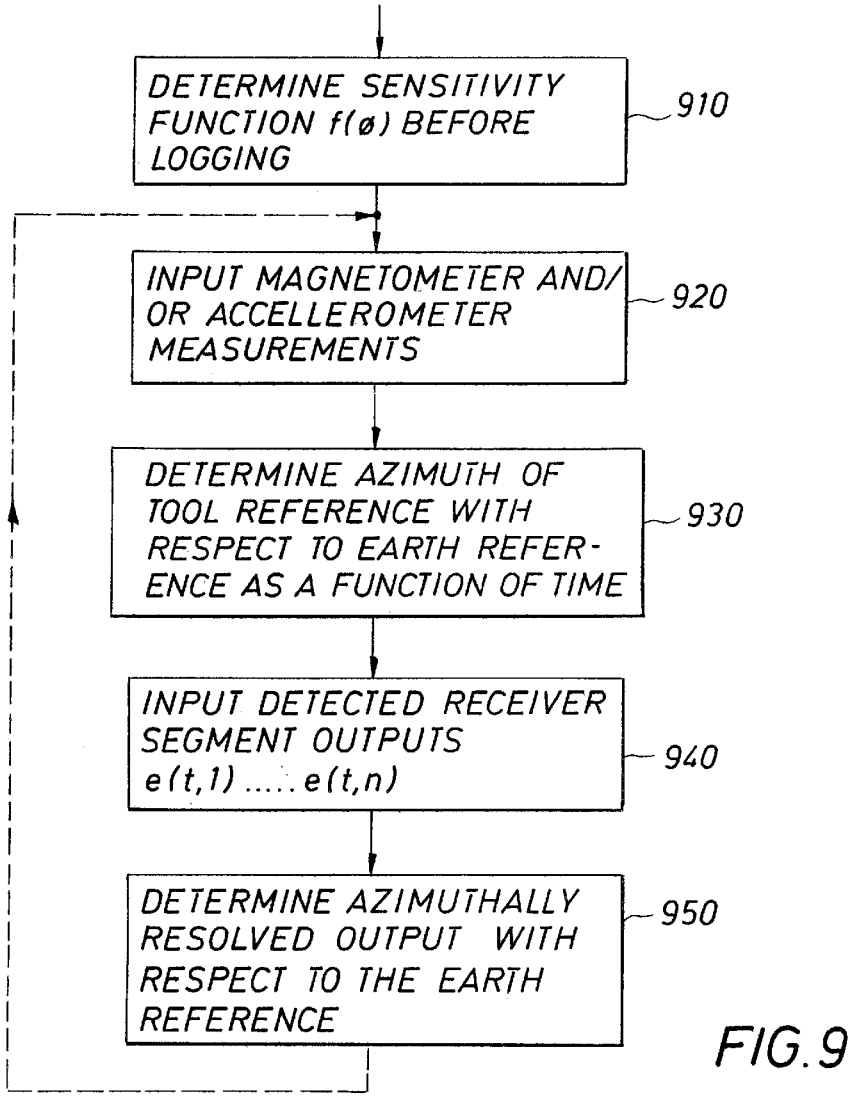
FIG. 9 is a flow diagram of a routine that can be used for programming a processor in accordance with an embodiment of the invention as set forth in the above-referenced copending U.S. patent application Ser. No. 08/880,343.

FIG. 9 is a flow diagram of a routine for controlling the processor 450, or other processor, to implement the processing to obtain azimuthally resolved NMR measurements with respect to an earth reference, in accordance with an embodiment of the invention as set forth in the above-referenced copending U.S. patent application Ser. No. 08/880,343. The block 910 represents the determination of the sensitivity function f(φ) which, as previously described, can be performed before logging. The magnetometer and/or accelerometer measurements are input, as represented by the block 920. The azimuth of tool reference, with respect to earth reference, can then be determined as a function of time using the formulas ξ=atan2(−My,Mx) or ζ=atan2(−Ay,Ax) described above, this being represented by the block 930. The detected receiver segment outputs e(t,1), e(t,2), . . . e(t,n) are input (block 940). Then, using equation (2), the azimuthally resolved output, with respect to the earth reference, can be determined, as represented by the block 950. For processing at further depths or time references, the block 920 is re-entered.

Figure 10:
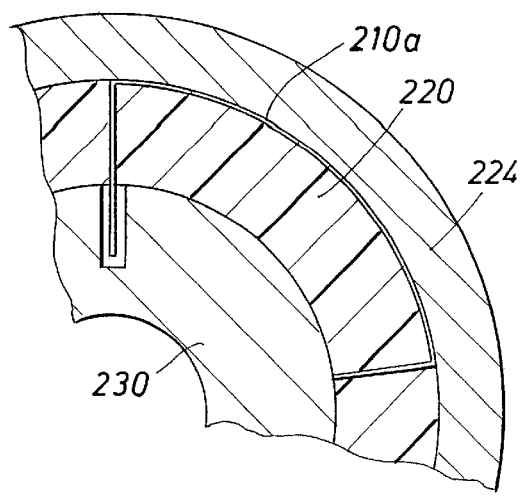
FIG. 10 is a cross-sectional partially broken away view of a receiving antenna on a logging device, in accordance with a further embodiment of the invention as set forth in the above-referenced copending U.S. patent application Ser. No. 08/880,343.

In an above described embodiment, there are four receiver coil segments, e.g. the coil segments 210a, 210b, 210c and 210d of FIGS. 3, 4,.5 and 6. One or a plurality of such segments can be utilized in receiving spin echo signals from a portion of the investigation region. When the logging device rotates, the rotating antenna segment or segments can provide azimuthally resolved NMR properties of the full 360 degree span of the surrounding formations. It is within contemplation of this invention to collect fewer echoes in accordance with the methods set forth in U.S. Pat. No. 5,705,927. It will be understood that there are trade-offs between resolution, signal strength, complexity and cost, when selecting the number, dimension, and configuration of antennas. In the embodiment of FIG. 10, in accordance with an embodiment of the invention as set forth in the above-referenced copending U.S. patent application Ser. No. 08/880,343, a single receiving antenna 210a (which may be, for example, one of the quadrant receiver antennas of the FIG. 5, 6 embodiment, which has a separate transmitting antenna 201) is shown and is mounted in the previously described manner. The Figure also shows drill collar 230, non-conductive material 220, and shield 224 which covers antenna 210a. The circuitry of FIG. 7 that is coupled with transmitting antenna 201 and receiving antenna 210a can be used in conjunction with this embodiment.

Figure 11:
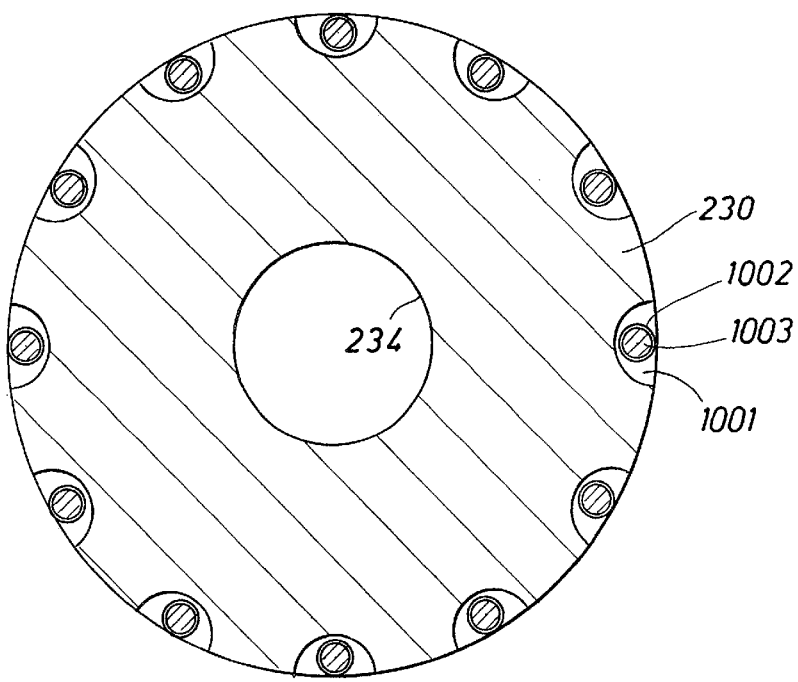
FIG. 11 is a cross-sectional view of a logging device in accordance with another embodiment of the invention as set forth in the above-referenced copending U.S. patent application Ser. No. 08/880,343.

FIG. 11 illustrates an embodiment of a logging device 200 (e.g. in FIG. 1) in accordance with a further form of the invention as set forth in the above-referenced copending U.S. patent application Ser. No. 08/880,343. In this embodiment, a plurality of receiver coil components 1002 are located in a respective plurality of axially oriented slots 1001 machined on the external surface of the drill collar 230. At least three such coils are preferred, with four or more being more preferred RF coils 1002 are wound on ferrite rods 1003. The axes of the ferrite rods 1003, the axes of the slots 1001, and the axis of the drill collar are all oriented in the same direction. The rf coils 1002 are covered by a nonmagnetic and insulating material such as ceramic, plastic, or rubber. Each coil is connected to the acquisition and processing electronics, which can be similar to that previously described in conjunction with FIG. 4, via a respective feed-through (as in FIG. 3). The rotationally symmetric transmitter field is produced by driving all coils in parallel. The transmitted field is rotationally symmetric at radial distances that are larger than the separation of the coils 1002. This embodiment leads to a relatively sturdy mechanical design, but generally with less receiver sensitivity than the prior embodiments.

In embodiments hereof to be treated subsequently, a region of generally uniform static field magnitude and polarization produced in the formations is relatively long in axial extent, and an advantage is that the rf antenna used to obtain azimuthally resolved measurements can also be made relatively long in the axial direction, thereby increasing the volume of spins ultimately sensed by the antenna and increasing signal-to-noise ratio. This increase tends to offset the decrease in the volume of spins that are obtained when the azimuthal range of investigation is limited to a sector that is a fraction of a full circumference. A magnet configuration of the type shown in FIGS. 2 and 5 can be utilized to obtain a radially polarized static magnetic field that is generally uniform over an investigation region and has a substantial axial extent. The useful properties of this type of static magnetic field can be improved using the techniques and structures disclosed in copending U.S. patent application Ser. No. 09/033,965, entitled "Nuclear Magnetic Resonance Apparatus And Method For Generating A Magnetic Field Having Straight Contour Lines In The Resonance Region", filed Mar. 3, 1998, and assigned to the same assignee as the present application, all teachings of said copending application being incorporated herein by reference. The just referenced copending application also discloses techniques and structures useful in conjunction herewith for producing an axially polarized static magnetic field that is generally uniform over an investigation region having a substantial axial extent. In the embodiments hereof to be described subsequently, the rf field is azimuthally polarized in the investigation region, so the static magnetic field in the investigation region is tailored to have a radial and/or axial polarization in the investigation region.

Figure 12:
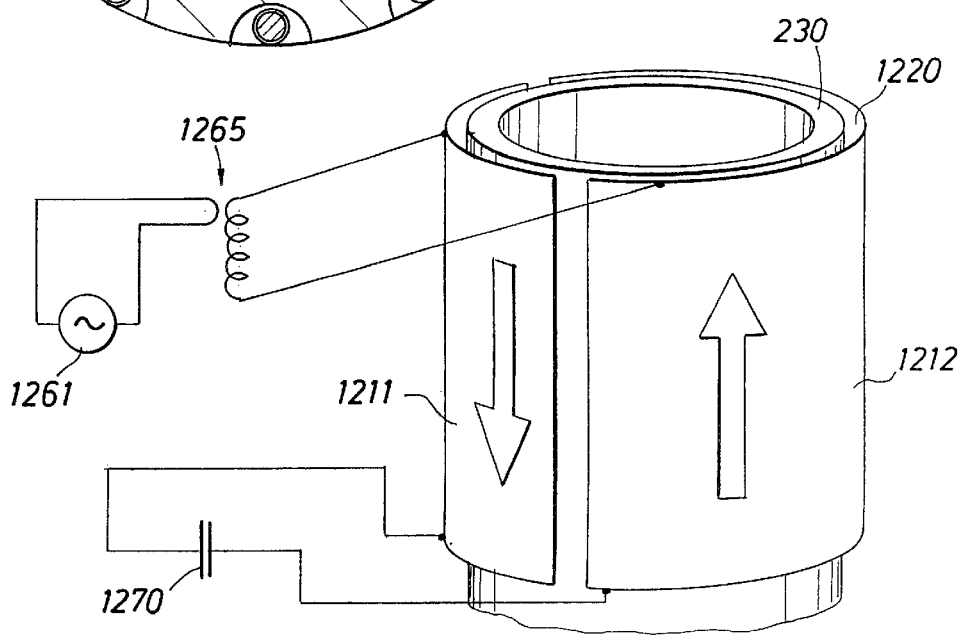
FIG. 12 is a schematic diagram of an antenna in accordance with an embodiment of the invention and which can be used in practicing an embodiment of the method of the invention.

FIG. 12 illustrates schematically an rf antenna in accordance with one embodiment of the invention. The drill collar (as in FIGS. 2 and 5) is represented at 230. [In a wireline embodiment, 230 can be the sonde pressure housing.] Electrodes 1211 and 1212 are thin plates of conductive metal, for example copper, disposed at a small radial distance outside the drill collar. In the illustrated embodiment the electrodes are cylindrical arcs with the smaller electrode 1211 preferably subtending an arc in the range 10 degrees to 120 degrees and the larger electrode preferably subtending an arc in the range 350 degrees to 240 degrees. [The total will be less than 360 degrees, as the longitudinal gaps between electrodes subtend at least a few degrees each.] An insulating material, such as fiberglass, or a ferrite (which can enhance the efficiency of the antenna), is disposed between the drill collar and the electrodes (in region 1220), or between the sonde pressure housing, if electrically conductive, and the electrodes. The plate electrodes are covered with a tough protective sleeve or shield (such as is shown at 1280 in FIG. 13) which may, for example, be formed of fiberglass, rubber, or a ceramic. An rf energizing source 1261 is inductively coupled (e.g. using transformer 1265) across the electrodes 1211 and 1212 at one longitudinal end thereof, and the electrodes are coupled at the opposing end, in this case by capacitor 1270, which passes the rf current). The capacitive and inductive elements can provide resonance at the desired frequency. If ferrite is not used in the antenna, additional inductance may need to be added externally. If the external inductance and tuning capacitance are located within the pressure housing, that would reduce the degree to which the antenna's resonant frequency changes with wellbore pressure variations. If desired, matching of the drive to the antenna could be further optimized by means of a second tap on the external inductor or by use of a capacitive voltage divider using the external capacitor and/or other suitable means. The large arrows in FIG. 12 shows the directions of the axial current flow for a particular instantaneous polarity of the rf source.

Figure 13:
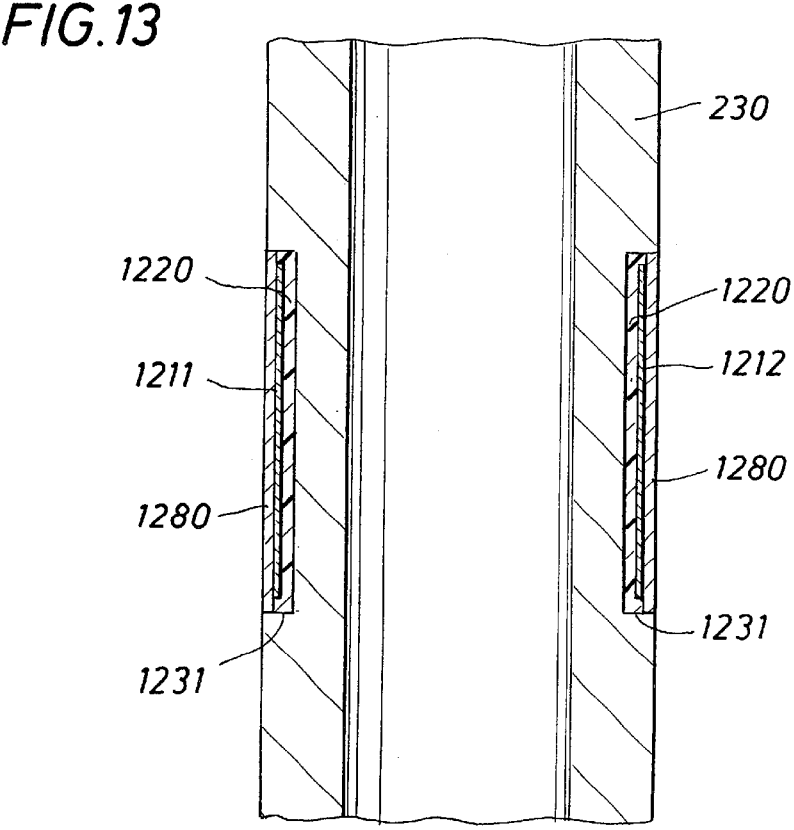
FIG. 13 is a cross-sectional view of the antenna of the FIG. 12 embodiment.

FIG. 13 shows a cross-section of the FIG. 12 antenna and illustrates an advantage that can accrue in this and other embodiments hereof by employing low profile antennas. The diagram of FIG. 13 shows the drill collar 230, insulating material 1220, conductive plate (1211 or 1212), and the protective sleeve or shield 1280, all contained in a recess or groove 1231 of the drill collar 230. [The circuitry and wiring, and the feedthroughs, which can be of conventional type, are not shown in the diagram.] In this embodiment the antenna is low profile and can be formed in an outer groove in the drill collar without necessarily reducing the inner diameter of the drill collar, which is ordinarily done to increase strength in a region of drill collar where the outer diameter has been recessed to provide an antenna. Reference can be made, for example, to FIGS. 2 and 5 which illustrate the decreased inner diameter of the drill collar at the antenna position. It will be understood that the configurations of FIGS. 2 and 5 might be implemented in a low profile configuration as shown in FIGS. 12 and 13 without reduction of the drill collar inner diameter, since the thickness of the antenna conductor(s) is relatively small. Furthermore, in a form of the embodiment of FIGS. 12, 13, the groove depth in the drill collar outer surface can be kept sufficiently small even with a substantial axial extent of the antenna that a reduction of the drill collar inner diameter may be dispensed with. The thin plates of conductive material used for the electrodes of the FIG. 12, 13 embodiment and subsequent embodiments also employing conductive plates, as well as other subsequent embodiments employing spirally wound coils, facilitate low profile antenna configurations that can permit dispensing with the reduction of the inner diameter of the drill collar at the rf antenna location.

In an example of fabrication of the plate antenna structure, the radial gap spacing between the drill collar (or pressure housing for a wireline implementation) and the electrodes can be built accurately, such as by wrapping high-temperature fiberglass onto the cylindrical collar/housing and machining it to the desired radius. For acoustic isolation, a layer of rubber or other elastomer is molded onto the drill collar. The layer of rubber is then wrapped with a sheet of copper which serves as a ground plane. The antenna structure is then loosely assembled and wrapped with a fiberglass or ferrite material. See e.g., U.S. Pat. No. 5,644,231. If desired, a layer of rubber or other elastomer can be molded onto the fiberglass for purposes of further magnetoacoustic isolation. Then, the conductive electrodes of copper or other suitable metal can be deposited onto the rubber or attached under pressure with epoxy. A further molding step can cover the electrodes with a layer of rubber and then with epoxy-or fiberglass and then with a layer of rubber for protection. The entire "sandwich" of layers can be covered with a tough, protective covering in the form of a tube or cylindrical shells. This protective-covering will preferably be nonmetallic, in order to allow sufficient transmission and reception of the NMR rf pulses and formation echo signals and to eliminate additional nearby sources of Johnson noise.

Figure 14:
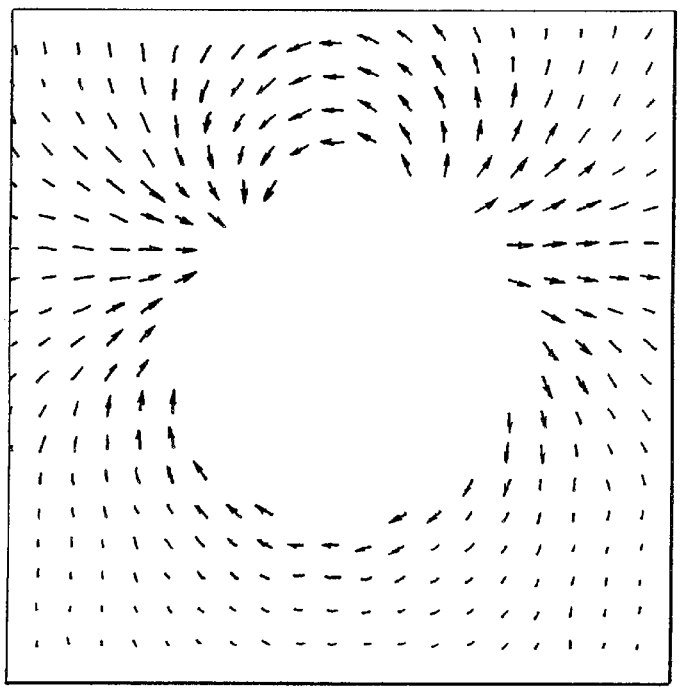
FIG. 14 illustrates the modeled rf magnetic field ($\overline{B}_1$) orientation and magnitude (given approximately by the lengths of the arrows) for the antenna geometry of FIG. 12, and a 60 degree angular extent of the smaller segment, which is pointing upward in this axial view.

FIG. 14 shows the modeled rf magnetic field ($\overline{B}_1$) orientation and magnitude (given approximately by the lengths of the arrows) for the antenna geometry of FIG. 12, a 60 degree angular extent of the smaller segment, which is pointing upward in this axial view. The fields inside the borehole (i.e., inside the empty circular spot in the center) are not shown. It can be noted that there is a strong front-to-back dissymmetry in the magnitude of the field. Also, there is a region of reasonable angular extent at the top of the plot where the rf field's orientation is nearly azimuthal at a constant radius. This region roughly defines the volume of spins contributing to the NMR signal. The thickness of the resulting arc-shaped shell of spins depends on the magnitude of the rf magnetic field $\overline{B}_1$ and on the spatial gradient of the static field $\overline{B}_0$.

Figure 15:
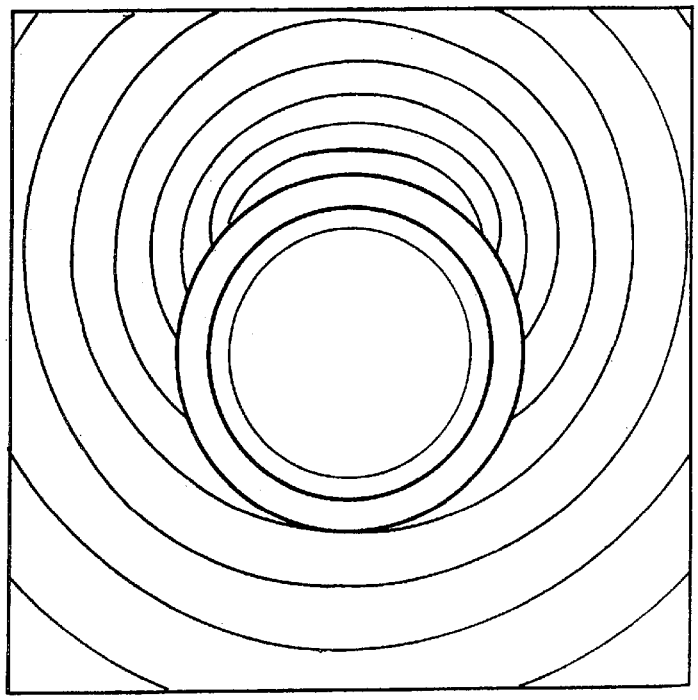
FIG. 15 shows contours of equal magnitude of the rf magnetic field ($\overline{B}_1$) for the same 60 degree antenna geometry shown in FIG. 14.

FIG. 15 shows contours of equal magnitude of the rf field ($\overline{B}_1$) for the same 60 degree antenna geometry shown in FIG. 14. The contours are geometrically spaced in terms of the magnitude of $\overline{B}_1$, so each additional contour (moving inward toward the center of the antenna) denotes a $\sqrt{2}$ greater field magnitude than the previous contour. Thus, moving outward by 6 contours corresponds to an 8-fold (or $20^{(6/2)}$ decrease in the field amplitude. The outer heavy-lined circle denotes the borehole diameter (same as in FIG. 14), and the inner heavy-lined circle denotes the diameter on which the antenna electrodes are located. The innermost (light-lined) circle denotes the diameter of the drill collar or (for wireline application) the sonde pressure housing, which is here concentric with the antenna electrodes.

Figure 16:
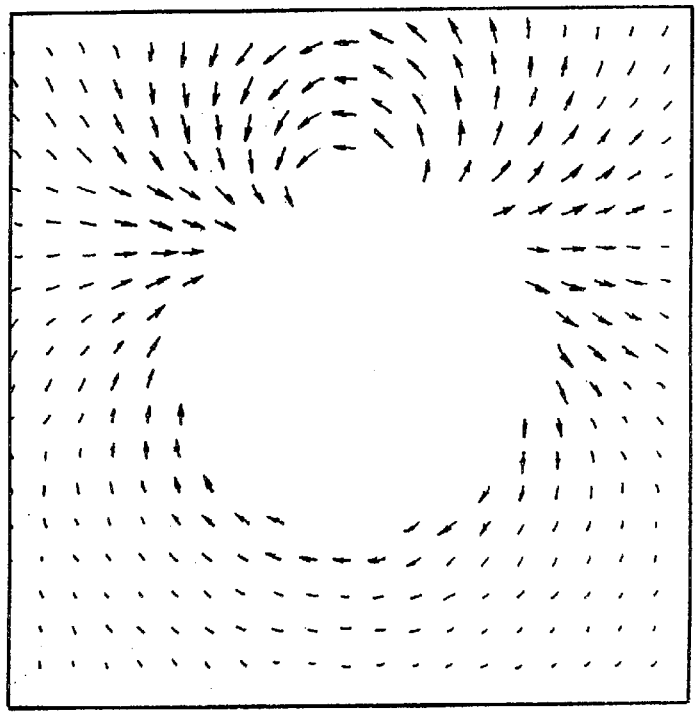
FIG. 16 shows the modeled rf magnetic field ($\overline{B}_1$) orientation and magnitude (given approximately by the lengths of the arrows) for the antenna geometry of FIG. 12, assuming in this case only a 30 degree angular extent of the smaller segment which is again pointing upward in this axial view.

FIG. 16 shows the modeled rf magnetic field ($\overline{B}_1$) orientation and magnitude (given approximately by the lengths of the arrows) for the antenna geometry of FIG. 12, assuming now only a 30 degree angular extent of the smaller segment, which is again pointing upward in this axial view. Again, the fields inside the borehole (i.e., inside the empty circular spot in the center) are not shown. Now the front-to-back dissymmetry in the magnitude of the field is somewhat more pronounced, and the region of interrogation at the top of the plot is somewhat smaller in angular extent. Thus, it is seen that varying the angular extent of the antenna electrode segment can provide considerable freedom in shaping the $\overline{B}_1$ field distribution.

Figure 17:
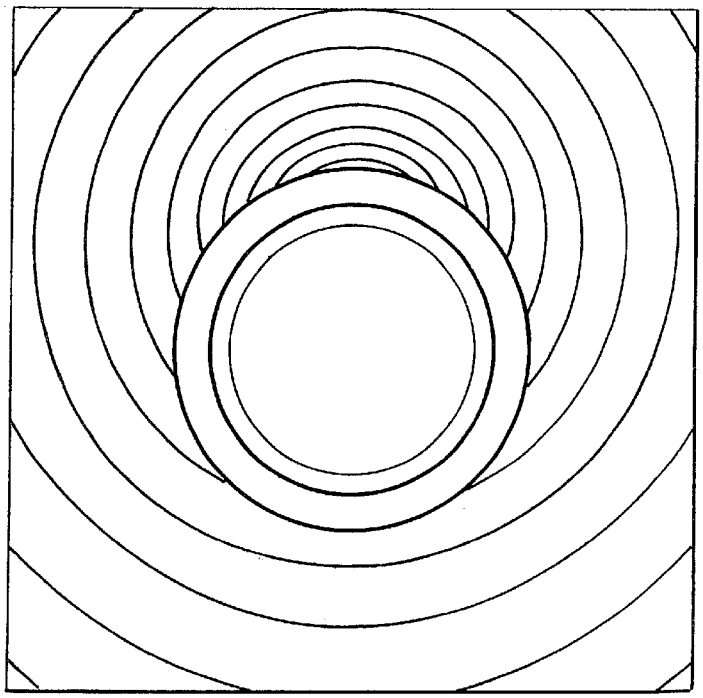
FIG. 17 shows contours of equal magnitude of the rf magnetic field ($\overline{B}_1$) for the same 30 degree antenna geometry shown in FIG. 16.

FIG. 17 shows contours of equal magnitude of the rf field ($\overline{B}_1$) for the same 30 degree antenna geometry shown in FIG. 16. Again, the contours are geometrically spaced in terms of the magnitude of $\overline{B}_1$, so each additional contour (moving inward toward the center of the antenna) denotes a $\sqrt{2}$ greater field magnitude than the previous contour. Thus, moving outward by 6 contours corresponds to an 8-fold (or $2^{(6/2)}$ decrease in the field amplitude. Again, the outer heavy-lined circle denotes the borehole diameter (same as in the previous Figures), and the inner heavy-lined circle denotes the diameter on which the antenna electrodes are located. The innermost (light-lined) circle denotes the diameter of the drill collar or (for wireline application) the sonde pressure housing, which is here concentric with the antenna electrodes.

Figure 18:
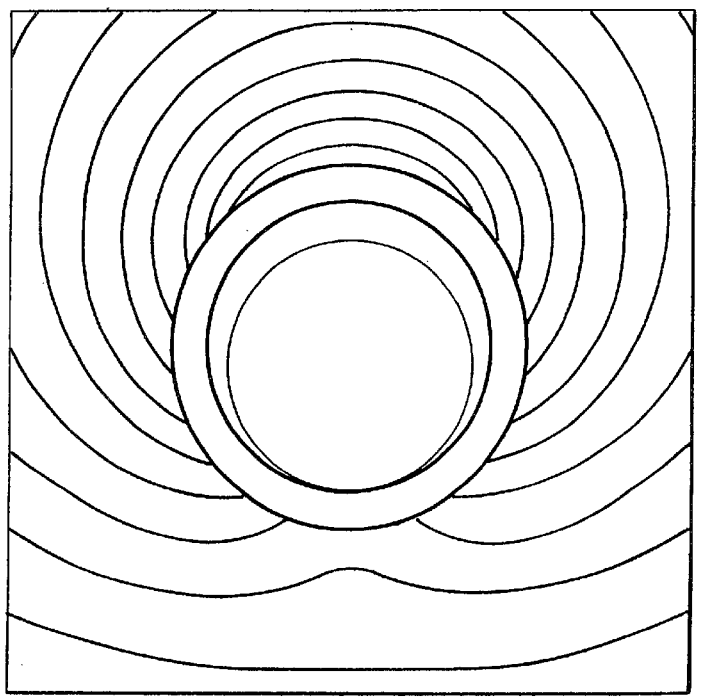
FIG. 18 show geometrically-spaced contours of equal magnitude of the rf magnetic field ($\overline{B}_1$) for the 60 degree antenna geometry of FIGS. 14 and 15, but with the drill collar or pressure housing no longer concentric with the electrodes.

FIG. 18 shows geometrically-spaced contours of equal magnitude of the rf field ($\overline{B}_1$) for the 60 degree antenna geometry of FIGS. 14 and 15. Now, however, the collar or pressure housing (shown by the innermost, light-lined circle) is no longer concentric with the electrodes but is, rather, eccentered by a substantial fraction (70%) of the radial gap spacing. Again, the contours are geometrically spaced in terms of the magnitude of $\overline{B}_1$, so each additional contour (moving inward toward the center of the antenna) denotes a $\sqrt{2}$ greater field magnitude than the previous contour. It can be noted that this eccentering increases the front-to-back dissymmetry in the field amplitude and therefore can be used as a control parameter to tailor the field geometry to the desired results. A similar effect can be realized by maintaining the two segments concentric with the drill collar or (for wireline application) the pressure housing but locating them at different radial distances from the center by, e.g., inserting them at different layers in a wrapped cylindrical composite structure.

Figure 19:
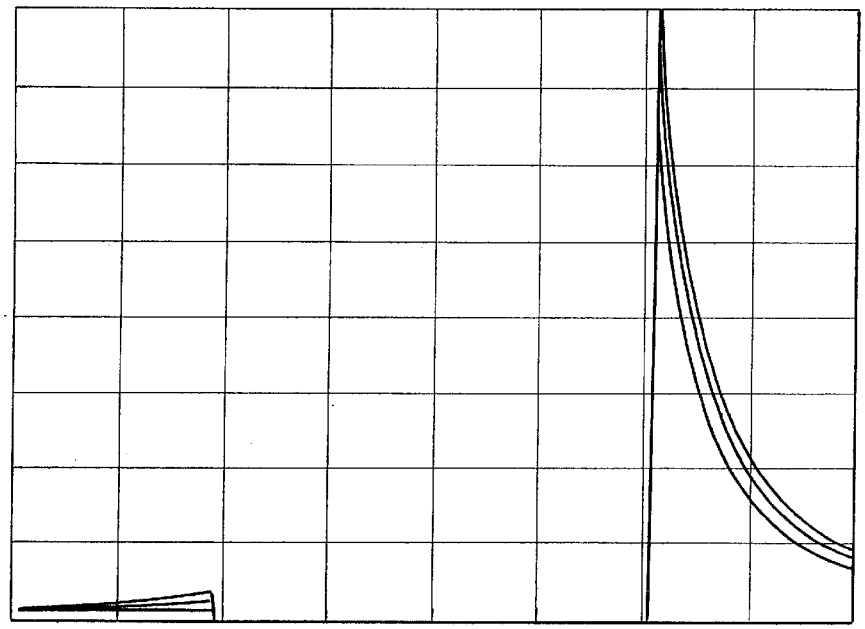
FIG. 19 shows the $\overline{B}_1$ rf field amplitude on a cross-section of the 60 degree antenna along its axis of symmetry; that is from bottom to top in FIG. 18.

On a linear scale, FIG. 19 shows the $\overline{B}_1$, rf field amplitude on a cross section of the 60 degree antenna along its axis of symmetry, i.e, from bottom to top in FIG. 18. As previously, only the fields outside the borehole radius are plotted. On the right side of FIG. 19 ("front" of antenna), the field amplitude is shown for the case of the drill collar/pressure housing being centered (lower curve), being eccentered by 40% of the radial gap distance (middle curve), and being eccentered by 70% of the radial gap distance (upper curve). On the left side of FIG. 19 ("back" of antenna), the field amplitude is shown for the centered case (upper curve), the 40% eccentered case (middle curve), and the 70% eccentered case (lower curve).

Figure 20:
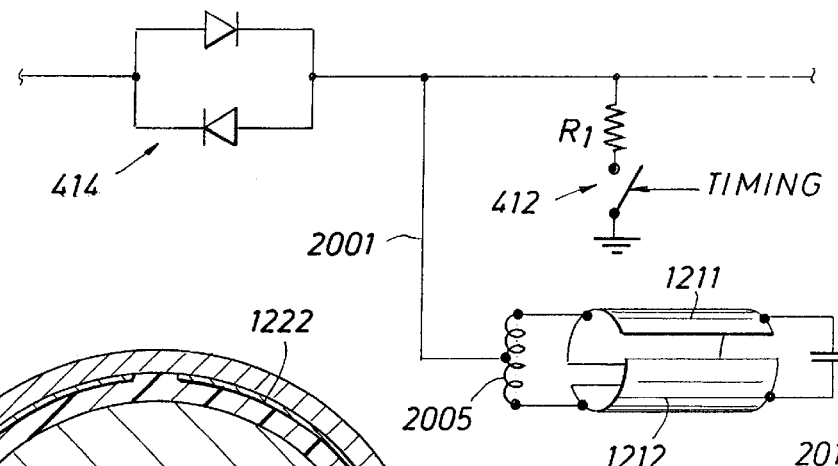
FIG. 20 is a schematic diagram of a type of circuit arrangement that can be utilized for transmitting and receiving from the rf antenna of FIG. 10 and other antennas hereof.

The embodiment of FIG. 12, and similar configurations, can generally be driven with circuitry of the type described above in conjunction with FIGS. 4 and 7. FIG. 20 illustrates a type of circuit arrangement that can be utilized for transmitting and receiving from the FIG. 12 type of rf antenna. The circuit elements 414, 412, and $R_1$ are the same as in FIG. 4, to provide perspective for the circuitry shown. The line 2001 (which caries the energizing and the received signals in this embodiment, is coupled with tapped inductor 2005 in impedance matching fashion, as previously described. [As above, a transformer drive can alternatively be utilized.] The inductor 2005 is coupled across the cylindrical arc shaped conductive plate electrodes 1211 and 1212, and capacitor 2015 is coupled across the other ends of the plate electrodes.

Figure 21:
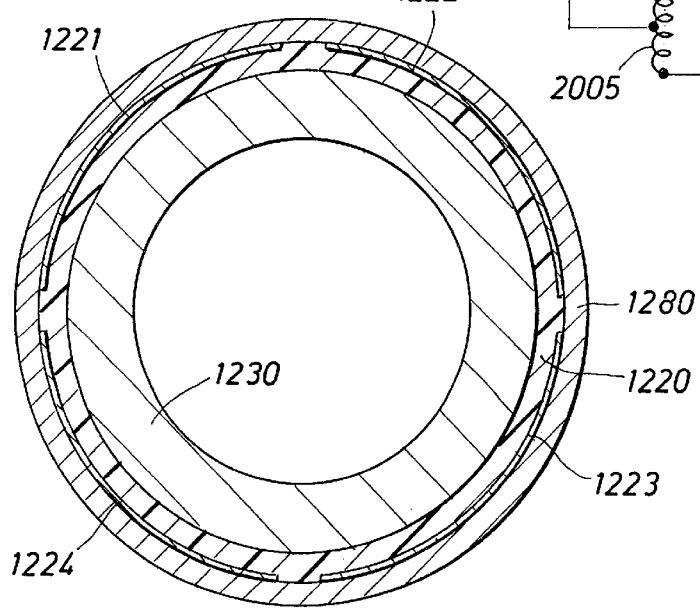
FIG. 21 is cross-sectional view of an rf antenna having four quadrants of arc shaped conductive electrodes for obtaining azimuthally resolved NMR signals.
Figure 22:
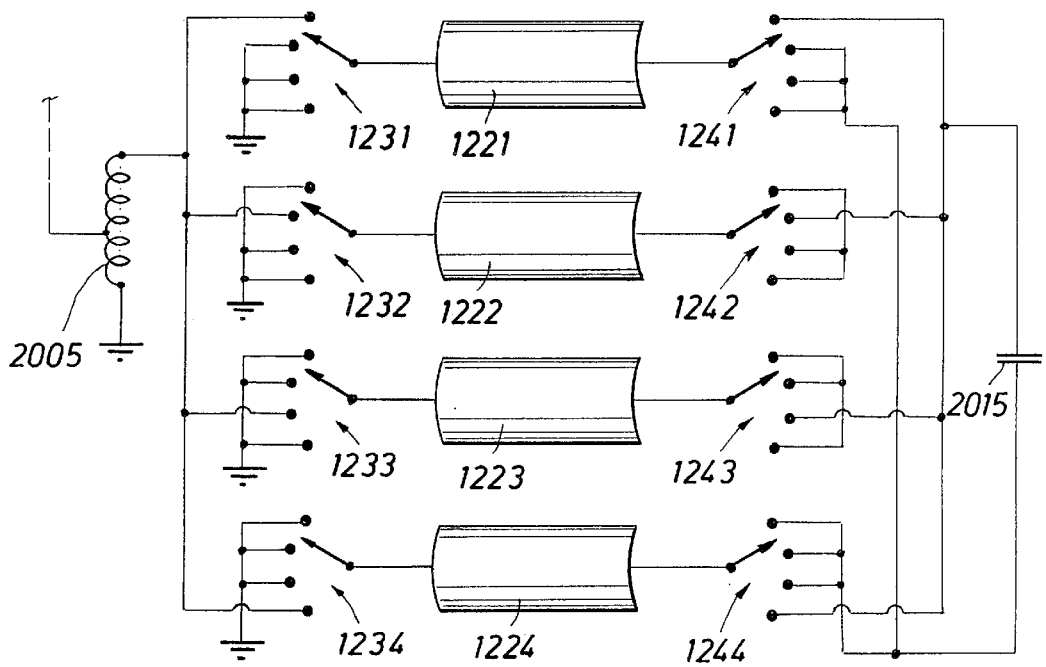
FIG. 22 is a schematic diagram of a type of circuitry that can be used in conjunction with the antenna of FIG. 21.

FIG. 21 illustrates an embodiment that utilizes four quadrants of arc shaped conductive plate electrodes (also shown individually in FIG. 22), for obtaining azimuthally resolved NMR signals as described in conjunction with FIGS. 3 and 4 above, but with the electrodes and magnetic fields associated with the conductive plate electrodes. The transmitting/receiving circuitry can be of the type described in conjunction with FIG. 4. One form of circuitry is illustrated in FIG. 22 which shows the individual conductive plates 1221, 1222, 1223, and 1224, which are coupled with the tapped inductor 2005 via electronic switches 1231, 1232, 1233 and 1234, respectively, and with capacitor 2015 via electronic switches 1241, 1242 1243, and 1244. As the switches cycle through their respective four positions (e.g. under control of processor 450), it is seen that the individual plate electrodes are coupled, one at a time, between inductor 2005 and one side of capacitor 2015, and that the other side of capacitor 2015 is coupled to each of the other plate electrodes for return in the opposite direction to ground reference potential. The azimuthally resolved NMR properties can then be obtained in the manner previously described.

Figures 23A, 23B:
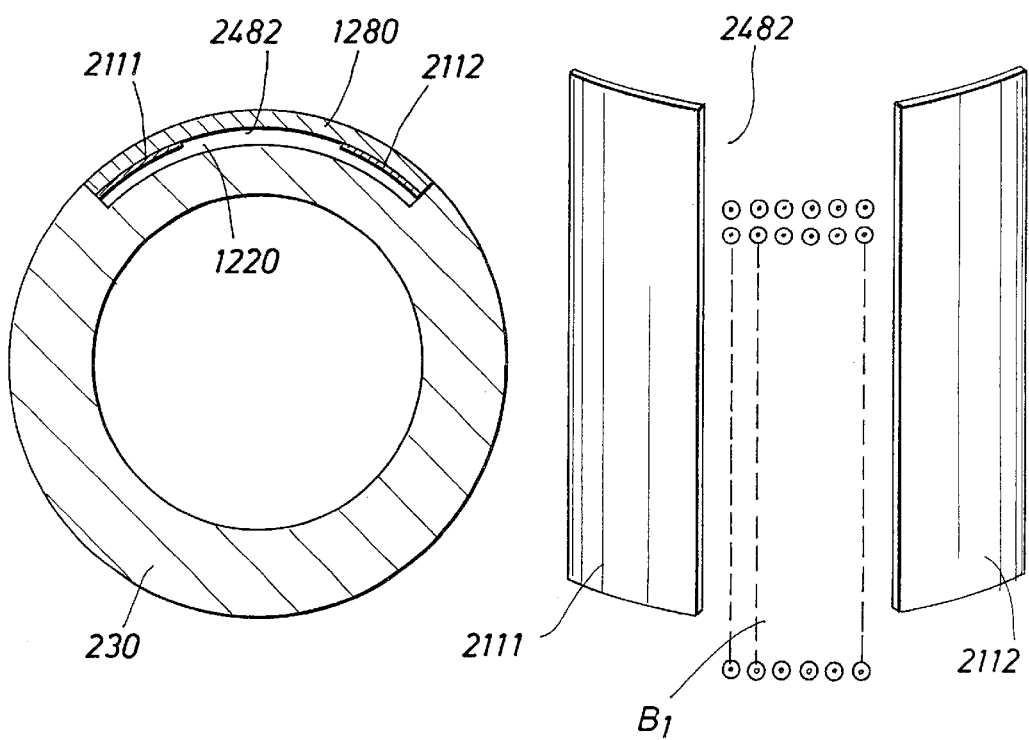
FIG. 23A is a cross-sectional view of an embodiment of a slot antenna that utilizes separated arc shaped plate electrodes.
FIG. 23B illustrates a simplified diagram of the electrodes in perspective, showing the radially polarized rf magnetic field that can be produced thereby.

Referring to FIG. 23A, there is shown a further embodiment wherein a substantial slot 2482 is provided between arc shaped plate electrodes 2111 and 2112, which can be coupled with the electronics as previously described, e.g. in FIG. 20. In this case, the investigation region is in front of the slot, and the rf magnetic field polarization is-radial. This is illustrated in FIG. 23B, which illustrates $\overline{B}_1$ in the investigation region as being out of (or into) the plane of the paper. Accordingly, in this case, the static magnetic field in the investigation region should have axial polarization (as described in the above referenced copending U.S. patent application Ser. No. 09/033,965), transverse, or azimuthal polarization. It will be understood that a plurality of antennas at different positions, as shown in FIG. 23A, could also be utilized (as in FIG. 21).

Figure 24A:
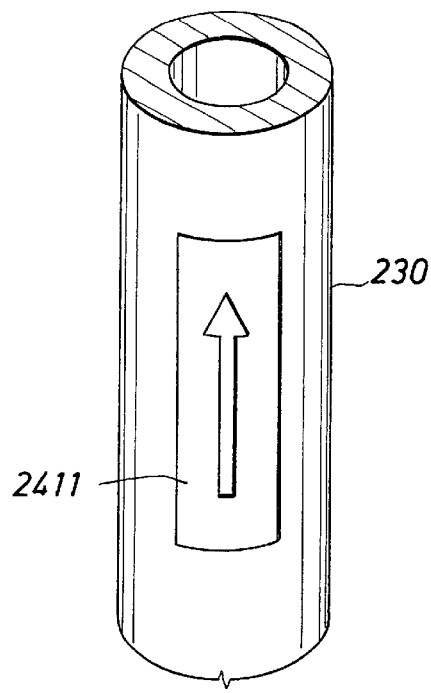
FIG. 24A illustrates an embodiment that utilizes a single plate electrode.
Figure 24B:
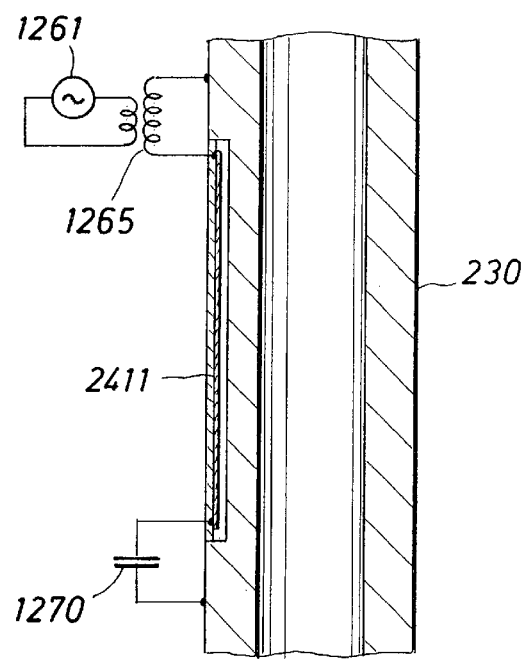
FIG. 24B illustrates how the plate electrode can be configured with circuitry for transmitting and receiving with return current path through the drill collar, if desired.

In the embodiment of FIGS. 24A and 24B, a single arc-shaped plate electrode 2411 is utilized. Here, as above, instantaneous current flow will be as shown by the large arrow, and the rf magnetic field polarization in the investigation region of the formations (generally opposing the electrode) will be azimuthally polarized (for use in conjunction with a static magnetic field polarization in the investigation region that is radial and/or axial). The energizing/receiving circuitry of the antenna can be provided floating, as above, or, as is shown in FIG. 24B, can use the drill collar 230 as a return path for the rf currents. The components 1261, 1265 and 1270 correspond to those of like reference numerals in FIG. 12.

Figure 25A:
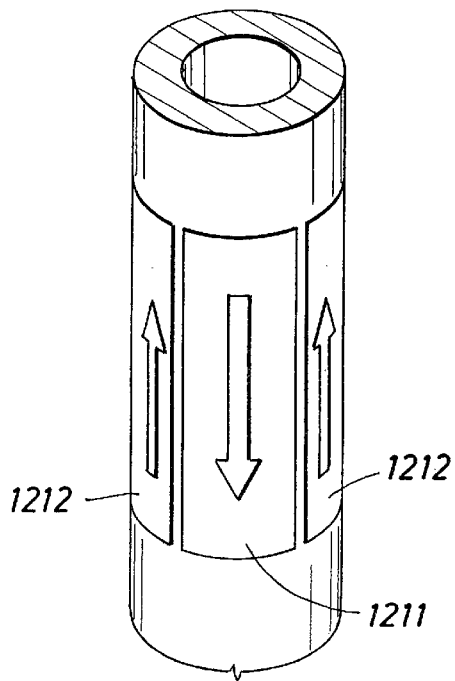
FIGS. 25A and 25B illustrates conceptually the replacement of arc-shaped plate electrodes with coils in which current flows primarily axially.
Figure 25B:
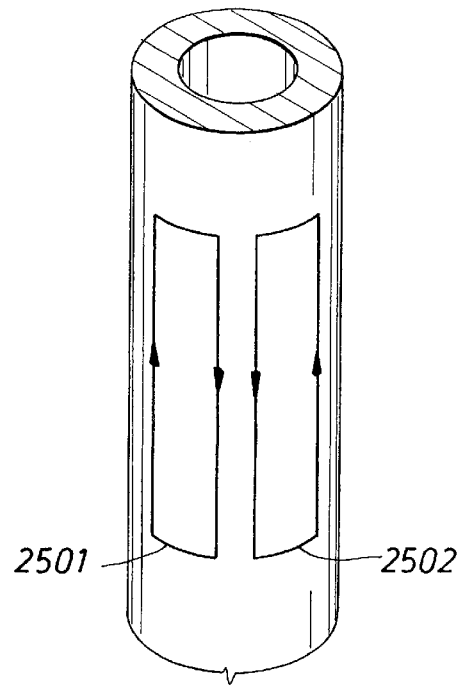

In embodiments of the invention to be described next, one or more coils are utilized to obtain rf magnetic fields ($\overline{B}_1$) that are azimuthally polarized in the investigation region, and which have substantial axial extent. The arc-shaped plate electrode(s) can be envisioned as being replaced by coil(s) wound on an axis that is perpendicular to the tool axis (which is, generally, the borehole axis), and in which current flows primarily axially, this being shown conceptually in FIGS. 25A and 25B. [The coils are wound to conform to the cylindrical arc of the drill collar contour, and preferably have an axial extent that is substantially greater than their circumferential extent. The instantaneous current flow in the plate electrodes as 1211 and 1212, as previously described, is illustrated in FIG. 25A, and the analogous current flow in the coils 2501 and 2502 is shown in FIG. 25B. The coil or coils can-be wound in spiral fashion (e.g. with increasing periphery dimensions for each successive turn, as shown conceptually in FIG. 26), to minimize coil thickness in the radial direction, and can be in the position(s) of the plate or plates as shown above in FIG. 13, with insulator at 1220 and protective covering at 1280 within the groove 1231 in drill collar 230. This facilitates a low profile type of structure, as first described above.

FIG. 27 illustrates a twin-loop multi-turn (8 turns being shown in this example), planar loop antenna, depicted unwrapped from the tool body. The antenna is shown as being driven by an rf source, V (with the sensed signals, during the receiving mode, being detected as first shown above, for example, in FIG. 4) at a tap to match the resonant antenna's resistance to line resistance $R_o$. The capacitor (or capacitors), C, tune the antenna.

Figure 28:
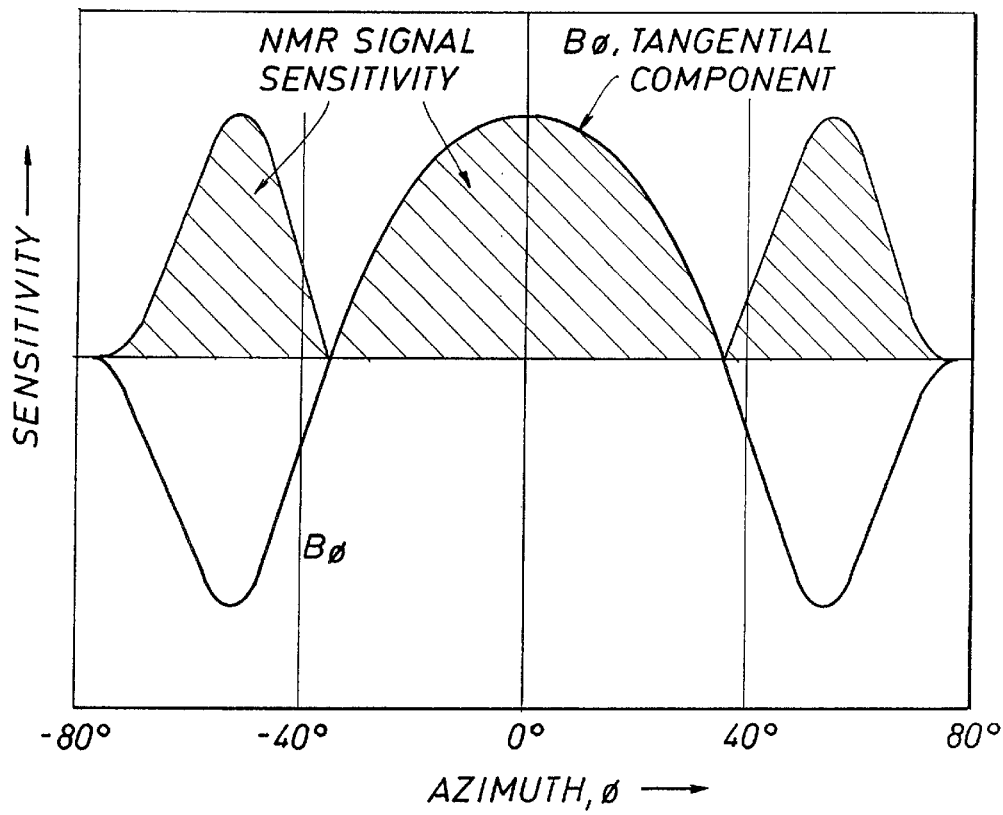
FIG. 28 is a diagram showing the rf magnetic field pattern of the antenna of FIG. 27, as a function of azimuth angle, as seen along the centerline of the antenna.

FIG. 28 shows the rf magnetic field pattern of the antenna of FIG. 27, as a function of azimuth angle, as seen along the centerline of the antenna. The magnetic field, $\overline{B}_\phi$, is a tangential component; i.e., as indicated above, polarized in the azimuth direction. The side lobes add to the NMR signal sensitivity, which is shown in the shaded regions in FIG. 28. It will be understood that a plurality of antennas can be employed, as represented, for example, in FIG. 23A (with the coil antennas substituted for the plate electrodes), and the array can be driven with circuitry similar to that of FIG. 4.

Figure 29:
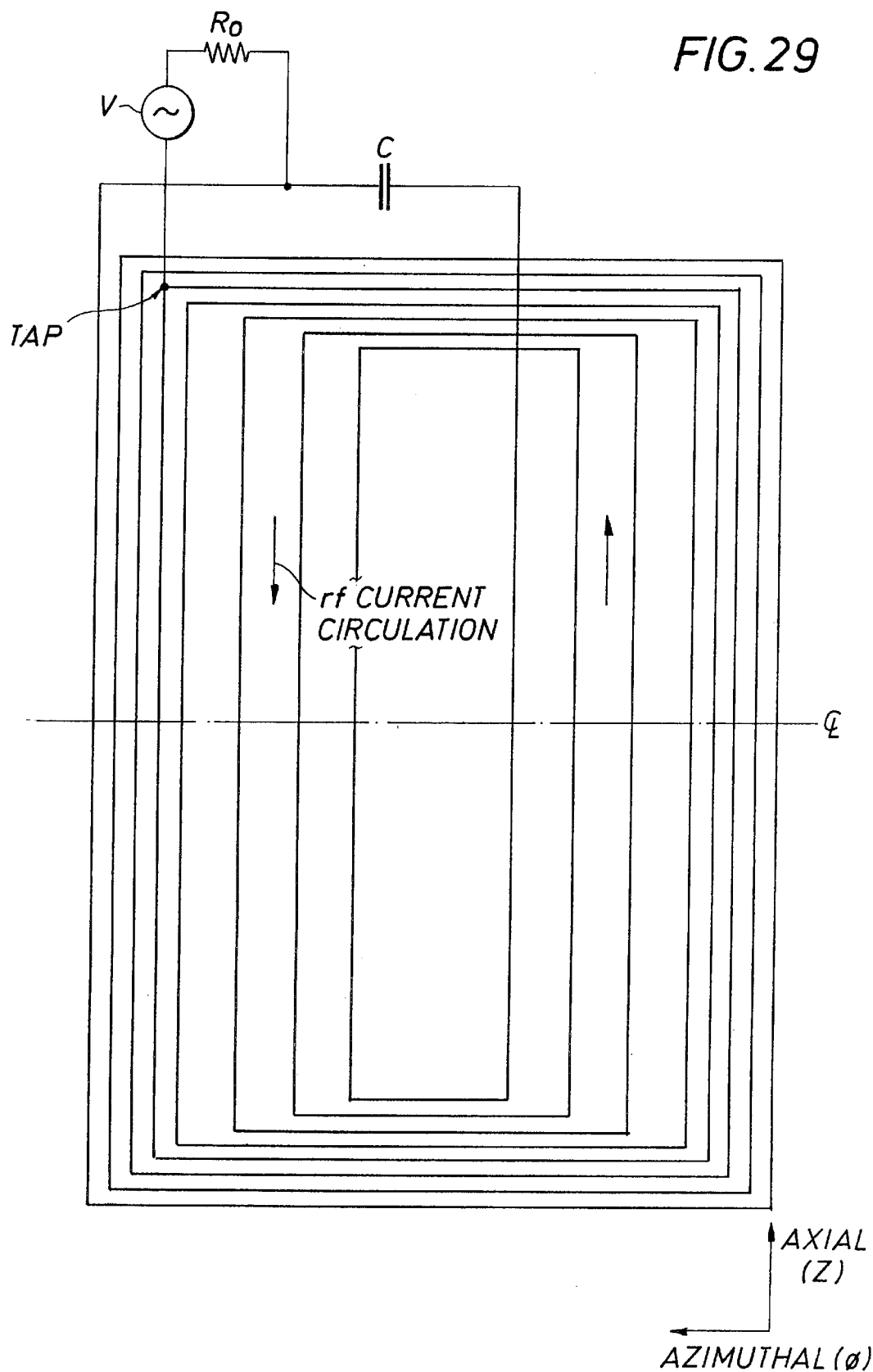
FIG. 29 shows a further embodiment of a multi-turn loop antenna, this antenna utilizing a single loop.
Figure 30:
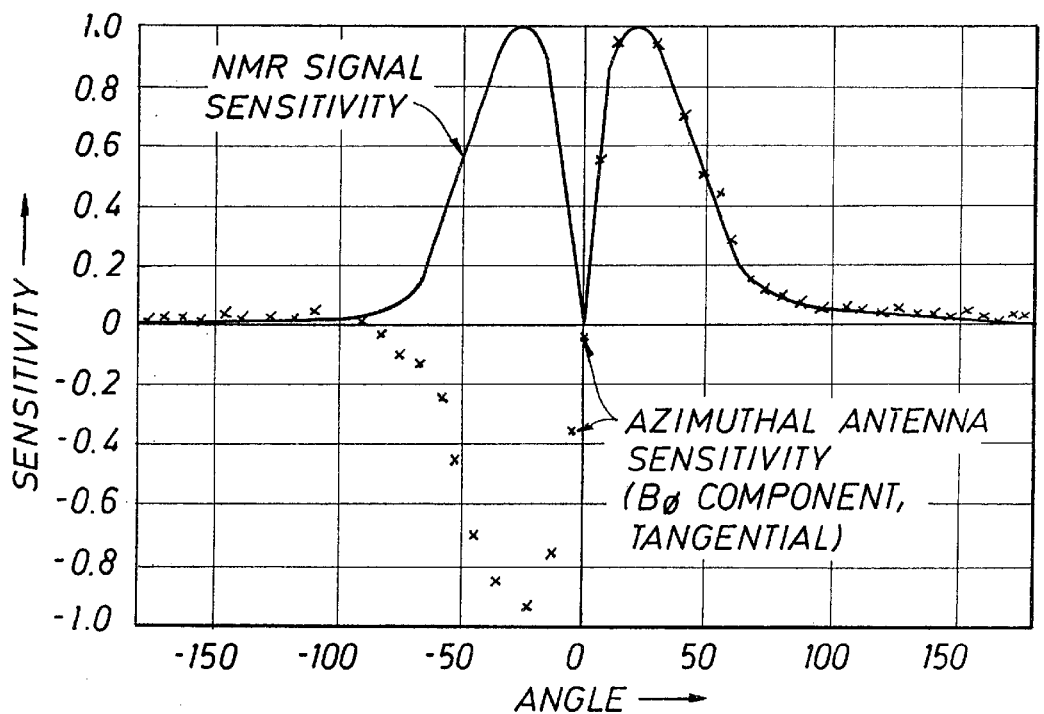
FIG. 30 is a diagram of the rf magnetic field pattern of the antenna of FIG. 29, as a function of azimuth angle, as seen along the centerline of the antenna.

FIG. 29 shows a further embodiment of a multi-turn planar loop antenna, unwrapped from the tool body. This antenna can be visualized as half the antenna of FIG. 27 (i.e., single loop), with eight turns being shown in-the single loop of this example. FIG. 30 shows the rf magnetic field pattern of the antenna of FIG. 29, as a function of azimuth angle, as seen along the centerline of the antenna. Again, the magnetic field, $\overline{B}_\phi$, is a tangential component, and the two lobes are of opposite polarity. The NMR signal sensitivity, which exhibits an approximately 90 degree pattern and good front-to-back isolation, is shown in the shaded area. Again, a plurality of antennas can be used, as in FIG. 23A, and driven using the FIG. 4 type of circuitry.

What is claimed is:

1. Apparatus for nuclear magnetic resonance logging that is mountable in a drill string for logging of formations surrounding a borehole, comprising:

a tubular drill collar having a generally cylindrical inner surface having an inner diameter and a generally cylindrical outer surface having an outer diameter;

first means in said drill collar for producing a first magnetic field;

second means in said drill collar for producing a second magnetic field; and means in said drill collar for receiving nuclear magnetic resonance signals from an investigation region in the formations;

said second means comprising an antenna disposed in a recess spanning an axial extent in said outer cylindrical surface, the outer surface of said drill collar having a diameter that is reduced from said outer diameter over the axial extent of said recess, and the inner surface of said drill collar having a diameter that is not substantially reduced from said inner diameter over the axial extent of said recess.

2. Apparatus as defined by claim 1, wherein said receiving means includes means coupled with said antenna for detecting signals induced in said antenna.

3. Apparatus as defined by claim 2, wherein said recess is an annular recess.

4. Apparatus as defined by claim 3, wherein said antenna comprises at least one generally cylindrical arc-shaped conductor plate in said recess.

5. Apparatus as defined by claim 3, wherein said antenna comprises a plurality of generally cylindrical arc-shaped conductor plates in said recess.

6. Apparatus as defined by claim 3, wherein said antenna comprises at least one multi-turn loop formed in a generally cylindrical arc shape in said recess.

7. Apparatus as defined by claim 2, wherein said antenna comprises at least one generally cylindrical arc-shaped conductor plate in said recess.

8. Apparatus as defined by claim 2, wherein said antenna comprises a plurality of generally cylindrical arc-shaped conductor plates in said recess.

9. Apparatus as defined by claim 2, wherein said antenna comprises at least one multi-turn loop formed in a generally cylindrical arc shape in said recess.

10. Apparatus as defined by claim 9, wherein said at least one multi-turn loop comprises a plurality of multi-turn loops.

11. Apparatus as defined by claim 9, wherein said loop has an axis that is substantially perpendicular to the longitudinal axis of said drill collar.

12. Apparatus as defined by claim 9, wherein said generally cylindrical arc shape of said loop is centered on a line oriented in the direction of the longitudinal axis of said drill collar.

* * * * *